US007888097B2

(12) United States Patent
Wu et al.

(10) Patent No.: US 7,888,097 B2
(45) Date of Patent: Feb. 15, 2011

(54) FORMULATION FOR ADENOVIRUS STORAGE

(75) Inventors: Zheng Wu, Sugar Land, TX (US);
Shuyuan Zhang, Sugar Land, TX (US)

(73) Assignee: Crucell Holland B.V., Leiden (NL)

( * ) Notice: Subject to any disclaimer, the term of this patent is extended or adjusted under 35 U.S.C. 154(b) by 454 days.

(21) Appl. No.: 11/926,854

(22) Filed: Oct. 29, 2007

(65) Prior Publication Data
US 2008/0102508 A1    May 1, 2008

Related U.S. Application Data

(60) Division of application No. 11/768,796, filed on Jun. 26, 2007, which is a continuation of application No. 09/941,296, filed on Aug. 28, 2001, now Pat. No. 7,235,391, which is a division of application No. 09/441,410, filed on Nov. 16, 1999, now Pat. No. 6,689,600.

(60) Provisional application No. 60/133,116, filed on May 7, 1999, provisional application No. 60/108,606, filed on Nov. 16, 1998.

(51) Int. Cl.
C12N 7/00    (2006.01)
C12N 1/04    (2006.01)

(52) U.S. Cl. ................. 435/235.1; 435/260; 435/320.1; 435/172.3; 435/239; 435/243

(58) Field of Classification Search .................... None
See application file for complete search history.

(56) References Cited

U.S. PATENT DOCUMENTS

| | | | |
|---|---|---|---|
| 4,352,883 A | 10/1982 | Lim | 435/178 |
| 4,725,547 A | 2/1988 | Sakamoto et al. | 435/239 |
| 4,797,368 A | 1/1989 | Carter et al. | 435/320.1 |
| 5,139,941 A | 8/1992 | Muzyczka et al. | 435/456 |
| 5,219,752 A | 6/1993 | Takazawa et al. | 435/394 |
| 5,552,309 A | 9/1996 | March | 435/456 |
| 5,607,851 A | 3/1997 | Pellegrini et al. | 435/236 |
| 5,744,304 A | 4/1998 | Munford | 435/6 |
| 5,789,244 A | 8/1998 | Heidrun et al. | 435/320.1 |
| 5,837,520 A | 11/1998 | Shabram et al. | 435/239 |
| 6,143,290 A | 11/2000 | Zhang et al. | 424/93.2 |
| 6,168,944 B1 | 1/2001 | Condon et al. | 435/239 |
| 6,194,191 B1 | 2/2001 | Zhang et al. | 435/239 |
| 6,194,210 B1 | 2/2001 | Leu et al. | 435/403 |
| 6,383,795 B1 | 5/2002 | Carrion et al. | 435/239 |
| 6,485,958 B2 | 11/2002 | Blanche et al. | 435/239 |
| 6,521,225 B1 * | 2/2003 | Srivastava et al. | 424/93.2 |
| 6,537,793 B2 | 3/2003 | Blanche et al. | 435/239 |
| 6,586,226 B2 | 7/2003 | Carrion et al. | 435/239 |
| 6,689,600 B1 | 2/2004 | Wu et al. | 435/235.1 |
| 6,726,907 B1 | 4/2004 | Zhang et al. | 424/93.2 |
| 7,125,706 B2 | 10/2006 | Zhang et al. | 435/235.1 |
| 2002/0018723 A1 | 2/2002 | Mera et al. | 417/222.2 |
| 2002/0094577 A1 | 7/2002 | Guirguis et al. | 436/18 |
| 2002/0177215 A1 | 11/2002 | Zhang et al. | 435/235.1 |
| 2003/0008375 A1 | 1/2003 | Zhang et al. | 435/235.1 |
| 2003/0166603 A1 | 9/2003 | Clayman | 514/44 |
| 2005/0089999 A1 | 4/2005 | Zhang et al. | 435/320.1 |
| 2006/0035857 A1 | 2/2006 | Clayman | 514/44 |
| 2007/0155008 A1 | 7/2007 | Zhang et al. | 435/320.1 |

FOREIGN PATENT DOCUMENTS

| | | |
|---|---|---|
| EP | 0273085 | 7/1988 |
| EP | 0475623 | 3/1992 |
| JP | 1279843 | 11/1989 |
| JP | 4-9338 | 1/1992 |
| WO | WO 93/18790 | 9/1993 |
| WO | WO 93/25224 | 12/1993 |
| WO | WO 94/06910 | 3/1994 |
| WO | WO 94/17178 | 8/1994 |
| WO | WO 95/06743 | 3/1995 |
| WO | WO 95/10601 | 4/1995 |
| WO | WO 95/19427 | 7/1995 |
| WO | WO 95/25789 | 9/1995 |
| WO | WO 96/09399 | 3/1996 |
| WO | WO 96/27677 | 9/1996 |
| WO | WO 96/32116 | 10/1996 |
| WO | WO 97/04803 | 2/1997 |
| WO | WO 97/08298 | 3/1997 |
| WO | WO 98/00524 | 1/1998 |
| WO | WO 98/22588 | 5/1998 |
| WO | WO 98/26048 | 6/1998 |

(Continued)

OTHER PUBLICATIONS

Aboud et al., "Rapid purification of extracellular and intracellular moloney murine leukemia virus," *Arch. Virol.*, 71:185-195, 1982.
Arap et al., "Replacement of the *p16/CDKN2* gene suppresses human glioma cell growth," *Cancer Res.*, 55:1351-1354, 1995.
Baichwal and Sugden, In: Kucherlapati R, ed. Gene transfer. New York: Plenum Press, 117-148, 1986.
Benvenisty and Reshef, "Direct introduction of genes into rats and expression of the genes," *Proc. Nat'l Acad Sci. USA*, 83:9551-9555, 1986.
Berg et al., "High-level expression of secreted proteins from cells adapted to serum-free suspension culture," *BioTechniques*, 14(6):972-978, 1993.

(Continued)

*Primary Examiner*—Robert A Zeman
(74) *Attorney, Agent, or Firm*—Fulbright & Jaworski L.L.P.

(57) ABSTRACT

The present invention addresses the need to improve the long-term storage stability (i.e. infectivity) of vector formulations. In particular, it has been demonstrated that for adenovirus, the use of bulking agents, cryoprotectants and lyoprotectants imparts desired properties that allow both lyophilized and liquid adenovirus formulations to be stored at 4° C. for up to 6 months and retain an infectivity between 60-100% of the starting infectivity.

23 Claims, 8 Drawing Sheets

FOREIGN PATENT DOCUMENTS

| | | |
|---|---|---|
| WO | WO 98/35554 | 8/1998 |
| WO | WO 99/12568 | 3/1999 |
| WO | WO 99/41416 | 8/1999 |
| WO | WO 99/54441 | 10/1999 |
| WO | WO 00/32754 | 6/2000 |
| WO | WO 00/34444 | 6/2000 |

PUBLICATIONS

Bett, "An efficient and flexible system for construction of adenovirus vectors with insertions or deletions in early regions 1 and 3," *Proc. Natl. Acad. Sci. USA*, 91(19):8802-8806, 1994.

Bussemakers et al., "Decreased expression of E-cadherin in the progression of rat prostatic cancer," *Cancer Res.*, 52:2916-2922, 1992.

Caldas et al., "Frequent somatic mutations and homozygous deletions of the p16 (MTS1) gene in pancreatic adenocarcinoma," *Nat. Genet.*, 8:27-32, 1994.

Cartwright, "Fermenter design for animal cell cultures," Animal Cells as Bioreactors, Cambridge University Press, 58-63, 1994.

Cartwright, T., *Animal cells as bioreactors*, in: Cambridge Studies in Biotechnology, Cambridge University Press, No. 11:58-63, 1994.

Carver et al., "Transgenic livestock as bioreactors: stable expression of human alpha-1-antitrypsin by a flock of sheep," *Biotechnology NY*, 11:1263-1270, 1993.

Casey et al., "Growth suppression of human breast cancer cells by the introduction of a wild-type p53 gene," *Oncogene*, 6:1791-1797, 1991.

Chen and Okayama, "High-efficiency transfection of mammalian cells by plasmid DNA," *Mol. Cell Biol.*, 7:2745-2752, 1987.

Cheng et al., "*p16* alterations and deletion mapping of 9p21-p22 in malignant mesothelioma," *Cancer Res.*, 54:5547-5551, 1994.

Cheung et al., "Cell-CAM105 isoforms with different adhesion functions are coexpressed in adult rat tissues and during liver development", *J. Biol. Chem.*, 268:6139-6146, 1993.

Cheung et al., "Structure and function of C-CAM1," *J. Biol. Chem.*, 268:24303-24310, 1993.

Cheung et al., "The cytoplaxmic domain of C-CAM is required for C-CAM-mediated adhesion function: studies of a C-CAM transcript containing an unspliced intron", *Biochem. J.*, 295:427-435, 1993.

Clarke, Peter, "Curriculum Vitae", Introgen Therapeutics Inc., (E1).

Coffin, "Retroviridae and their replication," in: *Virology*, Fields et al. (eds.), New York: Raven Press, pp. 1437-1500, 1990.

Complaint *Aventis Pharmaceuticals Products Inc. and Aventis Pharma, S.A.*, Plaintiffs, v. *Introgen Therapeutics, Inc.*, Defendant. Civil Action No. 01-451 from the U.S. District Court for the District of Delaware, Jun. 29, 2001.

Co-pending U.S. Appl. No. 08/975,519.

Corveleyn and Remon, "Maltodextrins as lyoprotectants in the lyophilization of a model protein, LDH," *Pharm. Res.*, 13:146-150, 1996.

Côté et al., "Study of Adenovirus Production in Serum-Free 293SF Suspension Culture by GFP-Expression Monitoring", Biotechnol. Prog., 13:709-714, 1997.

Coupar et al., "A general method for the construction of recombinant vaccinia virus expressing multiple foreign genes," *Gene*, 68:1-10, 1988.

Crooks et al., "Purification and analysis of infections virions and native non-structural antigens from cells infected with tick-borne encephalitis virus," *J. Chrom.*, 502:59-68, 1990.

Croyle et al., "Factors that influence stability of recombinant adenoviral preparations for human gene therapy," *Pharm. Dev. Technol.*, 3(3):373-383, 1998.

Dubensky et al,. "Direct transfection of viral and plasmid DNA into the liver or spleen of mice," *Proc. Nat. Acad. Sci. USA*, 81:7529-7533, 1984.

Edelman and Crossin, "Cell adhesion molecules: implications for a molecular histology," *Annu. Rev. Biochem.*, 60:155-190, 1991.

Edelman, "Cell adhesion and the molecular processes of morphogenesis," *Annu. Rev. Biochem.*, 54:135-169, 1985.

European Office Action, issued in European Patent Application No. 06025694.8, dated Jun. 14, 2007.

European Office Action, issued in European Patent Application No. 06012869.1, dated Jun. 15, 2007.

Fechheimer et al., "Transfection of mammalian cells with plasmid DNA by scrape loading and sonication loading," *Proc. Nat'l Acad. Sci. USA*, 84:8463-8467, 1987.

Ferkol et al., "Regulation of the phosphoenolpyruvate carboxykinase/human factor IX gene introduced into the livers of adult rats by receptor-mediated gene transfer," *FASEB J.*, 7:1081-1091, 1993.

Fraley et al., "Entrapment of a bacterial plasmid in phospholipid vesicles: Potential for gene transfer," *Proc. Nat'l Acad. Sci. USA*, 76:3348-3352, 1979.

Freshney, "Animal Cell Culture: a Practical Approach," Second Edition, Oxford/New York, IRL Press, Oxford University Press, 1992.

Fried and Bromberg, "Factors that affect the stability of protein-DNA complexes during gel electrophoresis," *Electrophoresis*, 18:6-11, 1997.

Frixen et al., "E-cadherin-mediated cell-cell adhesion prevents invasiveness of human carcinoma cells," *J. Cell Biol.*, 113:173-185, 1991.

Garnier et al., "Scale-up of the adenovirus expression system for the production of recombinant protein in human 293S cells," *Cytotechnol.*, 15:145-155, 1994.

Ghosh and Bachhawat, in: *Liver Diseases, Targeted Diagnosis and Therapy Using Specific Receptors and Ligands*, Wu G, Wu C (ed.), Marcel Dekker, New York, 87-104, 1991.

Giancotti and Ruoslahti, "Elevated levels of the $\alpha_5\beta_1$ fibronectin receptor suppress the transformed phenotype of Chinese hamster ovary cells," *Cell*, 60:849-859, 1990.

Gilbert, "Adaptation of cells to serum free culture for production of adenovirus vectors and recombinant proteins," *Williamsburg BioProcessing Conference*, Nov. 18-21, 1996.

Gopal, "Gene transfer method for transient gene expression, stable transfection, and cotransfection of suspension cell cultures," *Mol. Cell Biol.*, 5:1188-1190, 1985.

Graham and Prevec, "Manipulation of adenovirus vectors," in: *Methods in Molecular Biology: Gene Transfer and Expression Protocols 7*, (Murray, Ed.), Humana Press, Clifton, NJ, 109-128, 1991.

Graham and Van Der Eb, "A new technique for the assay of infectivity of human adenovirus 5 DNA," *Virology*, 52:456-467, 1973.

Graham et al, "Characteristics of a human cell line transformed by DNA from human adenovirus type 5," *J. Gen. Virol.*, 36:59-72, 1977.

Graham, "Growth of 293 Cells in Suspension Culture," *J. Gen. Virol.*, 68:937-940, 1987.

Green and Daesch, "Biochemical Studies on Adenovirus Multiplication II. Kinetics of Nucleic Acid and Protein Synthesis in Suspension Cultures," *Virology*, 13:169-176, 1961.

Green and Wold, "Human adenoviruses: growth, purification, and transfection assay," *Methods in Enzymology*, 58:425-435, 1979.

Griffiths, "Overview of cell culture systems and their scale-up," in: *Animal Cell Biotechnology*, vol. 3, p. 179-220, (Spier and Griffiths, eds.), Academic Press, London, 1986.

Griffiths, "Scaling-up of animal cell cultures," in: Animal Cell Cultures. A Practical Approach, $2^{nd}$ edition, (ed. Freshney), 3:47-93, 1992.

Hall et al., "Stabilizing effect of sucrose against irreversible denaturation of rabbit muscle lactate dehydrogenase," *Biophys. Chem.*, 57:47-54, 1995.

Harland and Weintraub, "Translation of mammalian mRNA injected into *Xenopus* oocytes is specifically inhibited by antisense RNA," *J. Cell Biol.*, 101:1094-1099, 1985.

Haruna et al., "Separation of adenovirus by chromatography on DEAE-cellulose," Virology, 13:264-267, 1961.

Hay et al., "Replication of adenovirus mini-chromosomes," *J. Mol. Biol.*, 175:493-510, 1984.

Hearing and Shenk, "Functional analysis of the nucleotide sequence surrounding the cap site for adenovirus type 5 region E1A messenger RNAs," *J. Mol. Biol.*, 167:809-822, 1983.

Hearing et al., "Identification of a repeated sequence element required for efficient encapsidation of the adenovirus type 5 chromosome," *J. Virol.*, 61:2555-2558, 1987.

Herman et al., "The effect of bulking agent on the solid-state stability of freeze-dried methylprednisolone sodium succinate," *Pharm. Res.*, 11:1467-1473, 1994.

Hermonat and Muzycska, "Use of adenoassociated virus as a mammalian DNA cloning vector: Transduction of neomycin resistance into mammalian tissue culture cells," *Proc. Nat'l Acad. Sci. USA*, 81:6466-6470, 1984.

Hollestein et al., "p53 mutations in human cancers," *Science*, 253:49-53 1991.

Hussussian et al., "Germline p16 mutations in familial melanoma," *Nature Genetics*, 15-21, 1994.

Huyghe et al., "Purification of a type 5 recombinant adenovirus encoding human p53 by column chromatography," *Hum. Gene Ther.*, 6:1403-1416,19956.

Jones and Shenk, "Isolation of deletion and substitution mutants of adenovirus type 5," *Cell*, 13:181-188, 1978.

Kamb et al., "A cell cycle regulator potentially involved in genesis of many tumor types," *Science*, 2674:436-440, 1994.

Kamb et al., "Analysis of the p16 gene (*CDKN2*) as a candidate for the chromosome 9p melanoma susceptibility locus," *Nature Genetics*, 8:22-26, 1994.

Kaneda et al., "Increased expression of DNA cointroduced with nuclear protein in adult rat liver," *Science*, 243:375-378, 1989.

Kato et al., "Expression of Hepatitis B virus surface antigen in adult rat liver," *J. Biol. Chem.*, 266:3361-3364, 1991.

Kawakubo et al., "Tissue plasminogen activator (t-PA) production by a high density culture of weakly adherent human embryonic kidney cells using a polyurethane-foam packed-bed culture system," *Appl. Microbiol. Biotechnol.*, 41:413-418, 1994.

Klein et al., "High-velocity microprojectiles for delivering nucleic acids into living cells," *Nature*, 327:70-73, 1987.

Kotani et al., "Improved methods of retroviral vector transduction and production for gene therapy," *Human Gene Therapy*, 5:19-28, 1994.

Kotani, "Serum-free production of adenoviral vectors for gene therapy," Williamsburg BioProcessing Conference, Nov. 18-21, 1996.

Kraft V., Tischer I, "Cell cycle-dependent multiplication of avian adenoviruses in chicken embryo fibroblasts," *Arch. Virol.*, 57: 243-54, 1978.

Larsson and Litwin, "The growth of polio virus in human diploid fibroblasts grown with cellulose microcarriers in suspension cultures," *Dev. Biol. Standard.*, 66:385-390, 1987.

Lentfer and Conde, "A rapid and inexpensive procedure for the purification of adenovirions," *Archives of Virology*, 56:189-193, 1978.

Levrero et al., "Defective and nondefective adenovirus vectors for expressing foreign genes in vitro and in vivo," *Gene*, 101:195-202, 1991.

Lin and Guidotti, "Cloning and expression of a cDNA coding for a rat liver plasma membrane ecto-ATpase," *J. Biol. Chem.*, 264:14408-14414, 1989.

Lu et al., "Coat protein interactions involved in tobacco mosaic tobamovirus cross-protection," *Virology*, 248:188-198, 1998.

Lueckel et al., "Formulations of sugars with amino acids or mannitol—influence of concentration ratio on the properties of the freeze-concentrate and the lyophilizate," *Pharm. Dev. Technol.*, 3:326-336, 1998.

Mann et al., "Construction of a retrovirus packaging mutant and its use to produce helper-free defective retrovirus," *Cell*, 33:153-159, 1983.

Mann et al., "Prospects for large scale production of thermolabile products using anchorage dependent cells," *Develop. Biol. Standard*, 46:289-294, 1980.

Massie et al., "Improved Adenovirus Vector Provides Herpes Simplex Virus Ribonuocleotide Reductase R1 and R2 Subunites Very Efficiently", Bio/Technology 13:602, 1995.

Matsuura et al., "Altered expression of e-cadherin in gastric cancer tissues and carcinomatous fluid," *Brit. J. Cancer*, 66:1122-1130, 1992.

McGrath et al., "Retrovirus purification: method that conserves envelope glycoprotein and maximizes infectivity," *J. Virol.*, 25:923-927, 1978.

Mercer, "Cell cycle regulation and the p53 tumor suppressor protein," *Critic. Rev. Eukar. Gene Express.* 2:251-263, 1992.

Mizrahi, "Production of human interferons—an overview," *Proc. Biochem.*, Aug. 9-12, 1983.

Montagnon, "Polio and rabies vaccines produced in continuous cell lines: a reality for vero cell line," *Develop. Biol. Standard.*, 70:27-47, 1989.

Mori et al., "Frequent somatic mutation of the *MTS1/CDK4I* (Multiple Tumor suppressor/Cyclin dependent Kinase 4 Inhibitor) gene in esophageal squamous cell carcinoma," *Cancer Res.*, 54:3396-3397, 1994.

Morris et al., "Serum-free production of adenoviral vectors for gene therapy," *Williamsburg BioProcessing Conference*, Nov. 18-21, 1996.

Nadeau et al., *Biotechnology and Bioengineering*, 51:613-623, 1996.

Nicolas and Rubenstein, "Vectors: a survey of molecular cloning vectors and their uses," in: *Vectors: A Survey of Molecular Cloning Vectors and Their Uses*, Rodriguez and Denhardt, (eds.), Stoneham: Butterworth, 493-513, 1988.

Nicolau and Sene, "Liposome-mediated DNA transfer in eukaryotic cells," *Biochem. Biophys. Acta*, 721:185-190, 1982.

Nicolau et al., "Liposomes as carriers for in vivo gene transfer and expression," *Methods Enzymol.*, 149:157-176, 1987.

Nilsson and Mosbach, "Immobilized animal cells," *Dev. Biol. Standard*, 66:183-193.

Nobori et al., "Deletions of the cyclin-dependent kinase-4 inhibitor gene in multiple human cancers," *Nature*, 368:753-756, 1995.

Notice of Opposition to a European Patent, Opposing European Patent No. EP 0968284, dated Sep. 18, 2007.

O'Neil and Balkovic, "Virus harvesting and affinity-based liquid chromatography," *Bio. Technol.*, 11:173-178, 1993.

Obrink, "C-CAM (cell-CAM 105)—a member of the growing immunogloublin superfamily of cell adhesion proteins," *BioEssays*, 13:227-233, 1991.

Odin and Obrink, "Quantitative determination of the organ distribution of the cell adhesion molecule cell-CAM 105 by radioimmunoassay," *Exp. Cell Res.*, 171:1-15, 1987.

Okamoto et al., "Mutations and altered expression of $p16^{INK4}$ in human cancer," *Proc. Nat'l Acad. Sci. USA*, 91:11045-11049, 1994.

Orlow et al., "Chromosome 9 allelic losses and microsatellite alterations in human bladder tumors," *Cancer Res.*, 54:2848-2851, 1994.

Paskind et al., "Dependence of moloney murine leukemia virus production on cell growth," *Virology*, 67:242-248, 1975.

Payment et al., in: *Biotechnology Current Progress*, ed. P.N. Cheremisinoff et al., Technomic Publishing, 1991.

Perales et al., "Gene transfer in vivo: sustained expression and regulation of genes introduced into the liver by receptor-targeted uptake," *Proc. Natl. Acad. Sci. USA*, 91:4086-4090, 1994.

Perrin et al., "An experimental rabies vaccine produced with a new BHK-21 suspension cell culture process: use of serum-free medium and perfusion-reactor system," *Vaccine*, 13(13): 1244-1250, 1995.

Petricciani, "Should continuous cell lines be used as substrates for biological products?" *Dev. Biol. Standard*, 66:3-12, 1985.

Phillips et al., "Experience in the cultivation of mammalian cells on the 8000 l scale," in: *Large Scale Mammalian Cell Culture* (Feder and Tolbert, eds.), Academic Press, Orlando, FL, U.S.A., 1985.

Potter et al., "Enhancer-dependent expression of human k immunoglobulin genes introduced into mouse pre-B lymphocytes by electroporation," *Proc. Nat'l Acad. Sci. USA*, 81:7161-7165, 1984.

U.S. Appl. No. 60/026,667, Entitled: "Method for the Production of Recombinant Adenoviruses," RPR File No. ST96021-U.S., Translated from the French by the Medical Documentation Service® Institute for Scientific Information® Philadelphia, Pennsylvania.

Racher et al., "Culture of 293 cells in different culture systems: cell growth and recombinant adenovirus production," *Biotechnology Techniques*, 9:169-174, 1995.

Renan, "Cancer genes: current status, future prospects, and applications in radiotherapy/oncology," *Radiother. Oncol.*, 19:197-218, 1990.

Ridgeway, "Mammalian expression vectors," in: Rodriguez RL, Denhardt DT, ed. Vectors: A survey of molecular cloning vectors and their uses. Stoneham: Butterworth, pp. 467-492, 1988.

Rippe et al., "DNA-mediated gene transfer into adult rat hepatocytes in primary culture," *Mol. Cell Biol.*, 10:689-695, 1990.

Roux et al., "A versatile and potentially general approach to the targeting of specific cell types by retroviruses: application to the infection of human cells by means of major histocompatibility complex class I and class II antigens by mouse ecotropic murine leukemia virus-derived viruses," *Proc. Nat'l Acad. Sci. USA*, 86:9079-9083, 1989.

Sagrera et al., "Study of the influence of salt concentration on Newcastle disease virus matrix protein aggregation," *Biochem. Mol. Biol. Int.*, 46:429-435, 1998.

Serrano et al., "Inhibition of ras-induced proliferation and cellular transformation by p16$^{INK4}$," *Science*, 267:249-252, 1995.

Shabram et al., "Analytical anion-exchange HPLC of recombinant type-5 adenoviral particles," *Human Gene Therapy*, 8:453-465, 1997.

Smith and Lee, "Large-scale isolation and partial purification of type C RNA viruses on hydroxyapatite," *Analytical Biochem.*, 86: 252-263, 1978.

Takahasi et al., "Wild-type but not mutant p53 suppresses the growth of human lung cancer cells bearing multiple genetic lesions," *Cancer Res.*, 52:2340-2342, 1992.

Temin, "Retrovirus vectors for gene transfer: efficient integration into and expression of exogenous DNA in vertebrate cell genomes," in: *Gene Transfer*, (Kucherlapati, ed.), Plenum Press, New York, pp. 149-188, 1986.

Tibbetts, "Viral DNA sequences from incomplete particles of human adenovirus type 7," *Cell*, 12:243-249, 1977.

Trepanier et al., *Journal of Virological Methods*, 3:201-211, 1981.

Tur-Kaspa et al., "Use of electroporation to introduce biologically active foreign genes into primary rat hepatocytes," *Mol. Cell Biol.*, 6:716-718, 1986.

Umbas et al., "Expression of the cellular adhesion molecule E-cadherin is reduced or absent in high-grade prostate cancer," *Cancer Res.*, 52:5104-5109, 1992.

van Wezel, "Growth of cell-strains and primary cells on micro-carriers in homogeneous culture," *Nature*, 216:64-65, 1967.

Vanlandschoot et al., "pH-dependent aggregation and secretion of soluble monomeric influenza hemagglutinin," *Arch. Virol.*, 143:227-239, 1998.

Vossen and Fried, "Sequestration stabilizes lac repressor-DNA complexes during gel electrophoresis," *Anal. Biochem.*, 245:85-92, 1997.

Wagner et al., "Transferrin-polycation conjugates as carriers for DNA uptake into cells", *Proc. Nat'l. Acad. Sci.*, 87(9):3410-3414, 1990.

Wagner et al., "Antisense gene inhibition by oligonucleotides containing C-5 propyne pyrimidines," *Science*, 260:1510-1513, 1990.

Wang et al., "High cell density perfusion culture of hybridoma cells for production of monoclonal antibodies in the celligen packed bed reactor," in: *Animal Cell Technology: Basic & Applied Aspects*, (Kaminogawa et al., eds), Kluwer Academic Publishers, Netherlands, vol. 5, pp. 463-469, 1993.

Wang et al., "Modified CelliGen-packed bed bioreactors for hybridoma cell cultures," *Cytotechnol.*, 9:41-49, 1992.

Wang et al., "Studies on High-Density Cultivation of Vero Cells with Biosilon Solid Microcarrier," *Chinese Journal of Biotechnology*, 12(2):119-129, 1996.

Watt et al., "Human prostate-specific antigen: structural and functional similarity with serine proteases," *Proc. Nat'l Acad Sci.*, 83(2):3166-3170, 1986.

Weinberg, "Tumor suppressor genes," *Science*, 254:1138-1146, 1991.

Wills and Menzel, "Adenovirus Vectors for Gene Therapy of Cancer," *J. of Cellular Biochem.*, Suppl: 17E, S216:206, 1993.

Wong et al., "Appearance of b-lactamase activity in animal cells upon liposome mediated gene transfer," *Gene*, 10:87-94, 1980.

Wu and Wu, "Evidence for targeted gene delivery to HepG2 hepatoma cells in vitro," *Biochemistry*, 27:887-892, 1988.

Wu and Wu, "Liver-directed gene," *Adv. Drug Delivery Rev.*, 12:159-167, 1993.

Wu and Wu, "Receptor mediated in vitro gene transfections by a soluble DNA courier system," *J. Biol. Chem*, 262:4429-4432, 1987.

Yang et al., "In vivo and in vitro gene transfer to mammalian somatic cells by particle bombardment," *Proc. Nat'l Acad. Sci. USA*, 87:9568-9572, 1990.

Zhang et al, "Adenovirus Inhibition of Cell Translation Facilitates Release of Virus Particles and Enhances Degradation of the Cytokeratin Network", Journal of Virology, 2544-2555, 1994.

Berns and Giraud, "Adenovirus and adeno-associated virus as vectors for gene therapy," *Ann NY Acad Sci.*, 772:95-104, 1995.

Berns, "Parvoviridae and their replication," in: *Fundamental Virology*, Fields and Knipe, eds. Second Edition, Chapter 32, pp. 817-837, 1991.

Croyle et al., "Development of formulations that enhance physical stability of viral vectors for gene therapy," *Gene Therapy*, 8:1281-1290, 2001.

Dulbecco and Vogt, "Plaque formation and isolation of pure lines with poliomyelitis viruses," *J Exp Med.*, 99(2):167-182, 1954.

Horwitz, "Adenoviridae and their replication," in: *Fundamental Virology*, Fields and Knipe, eds. Second Edition, Chapter 31, pp. 771-813, 1991.

Murphy and Kingsbury, "Virus taxonomy," in: *Fundamental Virology*, Fields and Knipe, eds. Second Edition, Chapter 2, pp. 28-30, 1991.

Robbins et al., "Viral vectors for gene therapy," *Trends Biotechnol.*, 16(1):35-40, 1998.

\* cited by examiner

FORMULATION FOR ADENOVIRUS STORAGE

This application is a divisional of co-pending U.S. patent application Ser. No. 11/768,796, filed Jun. 26, 2007, which is a continuation of U.S. patent application Ser. No. 09/941,296, filed Aug. 28, 2001 (now issued as U.S. Pat. No. 7,235,391), which is a divisional of U.S. patent application Ser. No. 09/441,410, filed Nov. 16, 1999 (now issued as U.S. Pat. No. 6,689,600), which claims the benefit of U.S. Provisional Patent Application Ser. No. 60/133,116, filed May 7, 1999, and U.S. Provisional Patent Application Ser. No. 60/108,606, filed Nov. 16, 1998. The entire contents of these applications are incorporated by reference.

BACKGROUND OF THE INVENTION

A. Field of the Invention

The present invention relates generally to the fields of molecular biology, virus production and gene therapy. More particularly, it concerns methods for the formulation of highly purified lyophilized and liquid adenovirus particles stable for long-term storage. An important embodiment of the present invention is the use of such long-term storage virus preparations for gene therapy treatments of viral disease, genetic disease and malignancies.

B. Description of Related Art

Viruses are highly efficient at nucleic acid delivery to specific cell types, while often avoiding detection by the infected hosts immune system. These features make certain viruses attractive candidates as gene-delivery vehicles for use in gene therapies (Robbins and Ghivizzani; 1998; Cristiano et al., 1998). Retrovirus, adenovirus, adeno-associated virus (AAV), and herpes simplex virus are examples of commonly used viruses in gene therapies. Each of the aforementioned viruses has its advantages and limitations, and must therefore be selected according to suitability of a given gene therapy (Robbins and Ghivizzani; 1998).

A variety of cancer and genetic diseases currently are being addressed by gene therapy. Cardiovascular disease (Morishita et al., 1998), colorectal cancer (Fujiwara and Tanaka, 1998), lung cancer (Roth et al., 1998), brain tumors (Badie et al., 1998), and thyroid carcinoma (Braiden et al., 1998) are examples of gene therapy treatments currently under investigation. Further, the use of viral vectors in combination with other cancer treatments also is an avenue of current research (Jounaidi et al., 1998).

Viral particles must maintain their structural integrity to be infectious and biologically active. The structural integrity of a viral vector often is compromised during the formulation process, thus precluding its use as a gene therapy vector. Adenoviruses for gene therapy traditionally have been formulated in buffers containing 10% glycerol. Formulated adenovirus is stored at <−60° C. to ensure good virus stability during storage. This ultra-low temperature storage not only is very expensive, but creates significant inconvenience for storage, transportation and clinic use. There is an urgent need to develop new formulation for adenovirus that can be stored at refrigerated condition.

Lyophilization has been used widely to improve the stability of various viral vaccine and recombinant protein products. It is expected that the long-term storage stability of adenovirus can be improved by reducing the residual water content (moisture) in the formulated product through lyophilization. However, there have not been reported studies on the lyophilization of live adenovirus for gene therapy.

Generally it is assumed that adenovirus will not maintain its infectivity when stored at refrigerated condition in a liquid form for extended period of time. As a result, there are no reported studies on formulating and storing adenovirus at refrigerated condition in a liquid form. Thus, there remains a need for long-term storage stable formulations of viral preparations.

SUMMARY OF THE INVENTION

The present invention addresses the need for improved, storage stable viral formulations, and methods for the production thereof, for use in gene therapy. In particular embodiments, a pharmaceutical adenovirus composition comprising adenovirus particles and pharmaceutical excipients, the excipients including a bulking agent and one or more protectants, wherein the excipients are included in amounts effective to provide an adenovirus composition that is storage stable. In preferred embodiments, the adenovirus composition has an infectivity of between 60 and 100% of the starting infectivity, and a residual moisture of less than about 5%, when stored for six months at 4° centigrade.

In one embodiment, the adenovirus composition is a freeze dried composition. In particular embodiments, the bulking agent in the freeze dried adenovirus composition forms crystals during freezing, wherein the bulking agent is mannitol, inositol, lactitol, xylitol, isomaltol, sorbitol, gelatin, agar, pectin, casein, dried skim milk, dried whole milk, silcate, carboxypolymethylene, hydroxyethyl cellulose, hydroxypropyl cellulose, hydroxypropyl methhylcellulose or methylcellulose.

In certain embodiments, the bulking agent in the freeze dried adenovirus composition is mannitol. In other embodiments the composition is further defined as an aqueous composition comprising mannitol in a concentration of from about 1% to about 10% (w/v). In another embodiment, the aqueous composition comprises the mannitol in a concentration of from about 3% to 8%. In a preferred embodiment, the aqueous composition comprises mannitol in a concentration of from about 5% to 7%.

In certain embodiments, the freeze dried composition is prepared from an aqueous composition comprising a bulking agent in a concentration of from about 1% to 10% (w/v). In other embodiments the freeze dried composition is prepared from an aqueous composition comprising a bulking agent in a concentration of from about 3% to 8%. In yet other embodiments, the freeze dried composition is prepared from an aqueous composition comprising a bulking agent in a concentration of from about 5% to 7%.

In particular embodiments, pharmaceutical excipients serve as a protectants. In one embodiment, the protectant is further defined as a cryoprotectant. In certain embodiments, the cryoprotectant is a non-reducing sugar. In particularly defined embodiments the non-reducing sugar is sucrose or trehalose. In preferred embodiments the non-reducing sugar is sucrose.

In certain embodiments, the composition is further defined as an aqueous composition comprising a non-reducing sugar in a concentration of from about 2% to about 10% (w/v). In other embodiments, the aqueous composition comprises the sugar in a concentration of from about 4% to 8%. In still other embodiments, the aqueous composition comprises the sugar in a concentration of from about 5% to 6%.

In one embodiment, the freeze dried composition is prepared from an aqueous composition comprising a non-reducing sugar in a concentration of from about 2% to 10% (w/v). In other embodiments, the freeze dried composition is prepared from an aqueous composition comprising a non-reducing sugar in a concentration of from about 4% to 8%. In yet other embodiments, the freeze dried composition is prepared from an aqueous composition comprising a non-reducing sugar in a concentration of from about 5% to 6%.

In another embodiment, the cryoprotectant is niacinamide, creatinine, monosodium glutamate, dimethyl sulfoxide or sweet whey solids.

In certain embodiments, the protectant includes a lyoprotectant, wherein the lyoprotectant is human serum albumin, bovine serum albumin, PEG, glycine, arginine, proline, lysine, alanine, polyvinyl pyrrolidine, polyvinyl alcohol, polydextran, maltodextrins, hydroxypropyl-beta-cyclodextrin, partially hydrolysed starches, Tween-20 or Tween-80. In a preferred embodiment, the lyoprotectant is human serum albumin.

In certain embodiments, the composition is further defined as an aqueous composition comprising the lyoprotectant in a concentration of from about 0.5% to about 5% (w/v). In another embodiment, the aqueous composition comprises the lyoprotectant in a concentration of from about 1% to about 4%. In still another embodiment, the aqueous composition comprises the lyoprotectant in a concentration of from about 1% to about 3%.

In particular embodiments, the freeze dried composition is prepared from an aqueous composition comprising a lyoprotectant in a concentration of from about 0.5% to 5% (w/v). In other embodiments, the freeze dried composition is prepared from an aqueous composition comprising a lyoprotectant in a concentration of from about 1% to 4%. In another embodiment, the freeze dried composition is prepared from an aqueous composition comprising a lyoprotectant in a concentration of from about 1% to 3%.

In one embodiment, pharmaceutical excipients defined as protectants, comprise both a lyoprotectant and a cryoprotectant.

Also contemplated in the present invention is an aqueous pharmaceutical adenovirus composition comprising a polyol in an amount effective to promote the maintenance of adenoviral infectivity. In one embodiment, adenoviral infectivity of the adenovirus polyol composition is further defined as maintaining an infectivity of about 70% PFU/mL to about 99.9% PFU/mL of the starting infectivity when stored for six months at 40 centigrade. In preferred embodiments, adenoviral infectivity is about 80% to 95% PFU/mL of the starting infectivity when stored for six months at 40 centigrade.

In the context of the present invention, a polyol is defined as a polyhydric alcohol containing two or more hydroxyl groups. In certain embodiments, the polyol is glycerol, propylene glycol, polyethylene glycol, sorbitol or mannitol, wherein the polyol concentration is from about 5% to about 30% (w/v). In other embodiments, the polyol concentration is from about 10% to about 30%. In yet other embodiments, the polyol concentration is about 25%.

In a preferred embodiment, the aqueous pharmaceutical adenovirus composition comprises a polyol in an amount effective to promote the maintenance of adenoviral infectivity, wherein the polyol is glycerol, included in a concentration of from about 5% to about 30% (w/v).

In other embodiments, the aqueous pharmaceutical adenovirus composition comprising a polyol in an amount effective to promote the maintenance of adenoviral infectivity further comprises an excipient in addition to the polyol, wherein the excipient is inositol, lactitol, xylitol, isomaltol, gelatin, agar, pectin, casein, dried skim milk, dried whole milk, silicate, carboxypolymethylene, hydroxyethyl cellulose, hydroxypropyl cellulose, hydroxypropyl methhylcellulose, methylcellulose, sucrose, dextrose, lactose, trehalose, glucose, maltose, niacinamide, creatinine, monosodium glutamate dimethyl sulfoxide, sweet whey solids, human serum albumin, bovine serum albumin, PEG, glycine, arginine, proline, lysine, alanine, polyvinyl pyrrolidine, polyvinyl alcohol, polydextran, maltodextrins, hydroxypropyl-beta-cyclodextrin, partially hydrolysed starches, Tween-20 or Tween-80.

In further defined embodiments, the aqueous pharmaceutical adenovirus composition comprising a polyol further comprises in addition to the polyol at least a first and a second excipient, wherein the second excipient is different the first excipient, and the excipient is inositol, lactitol, xylitol, isomaltol, gelatin, agar, pectin, casein, dried skim milk, dried whole milk, silicate, carboxypolymethylene, hydroxyethyl cellulose, hydroxypropyl cellulose, hydroxypropyl methhylcellulose, methylcellulose, sucrose, dextrose, lactose, trehalose, glucose, maltose, niacinamide, creatinine, monosodium glutamate dimethyl sulfoxide, sweet whey solids, human serum albumin, bovine serum albumin, PEG, glycine, arginine, proline, lysine, alanine, polyvinyl pyrrolidine, polyvinyl alcohol, polydextran, maltodextrins, hydroxypropyl-beta-cyclodextrin, partially hydrolysed starches, Tween-20 or Tween-80.

In another embodiment of the present invention, a method for the preparation of a long-term, storage stable adenovirus formulation, comprising the steps of providing adenovirus and combining the adenovirus with a solution comprising a buffer, a bulking agent, a cryoprotectant and a lyoprotectant; and lyophilizing the solution, whereby lyophilization of the solution produces a freeze-dried cake of the adenovirus formulation that retains high infectivity and low residual moisture.

In particular embodiments, the bulking agent used for preparing the freeze dried adenovirus formulation is mannitol, inositol, lactitol, xylitol, isomaltol, sorbitol, gelatin, agar, pectin, casein, dried skim milk, dried whole milk, silcate, carboxypolymethylene, hydroxyethyl cellulose, hydroxypropyl cellulose, hydroxypropyl methhylcellulose or methylcellulose. In preferred embodiments, the bulking agent is mannitol, wherein mannitol comprises about 0.5% to about 8% (w/v) of the formulation.

In other embodiments, the cryoprotectant used for preparing the freeze dried adenovirus formulation is sucrose, dextrose, lactose, trehalose, glucose, maltose, niacinamide, creatinine, monosodium glutamate dimethyl sulfoxide or sweet whey solids. In preferred embodiments, the cryoprotectant is sucrose, wherein sucrose comprises about 2.5% to about 10% (w/v) of said formulation.

In further embodiments, the lyoprotectant used for preparing the freeze dried adenovirus formulation is human serum albumin, bovine serum albumin, PEG, glycine, arginine, proline, lysine, alanine, polyvinyl pyrrolidine, polyvinyl alcohol, polydextran, maltodextrins, hydroxypropyl-beta-cyclodextrin, partially hydrolysed starches, Tween-20 or Tween-80. In preferred embodiments, the lyoprotectant is human serum albumin.

In other embodiments, the buffer used for preparing the freeze dried adenovirus formulation is Tris-HCl, TES, HEPES, mono-Tris, brucine tetrahydrate, EPPS, tricine, or histidine, wherein the buffer is present in the formulation at a concentration at about 1 mM to 50 mM. In one preferred embodiment, the buffer used for preparing the freeze dried adenovirus formulation is Tris-HCl, wherein the Tris-HCl is included in a concentration of from about 1 mM to about 50 mM. In another embodiment, the Tris-HCl is included in a concentration of from about 5 mM to about 20 mM. In still other embodiments, the freeze dried adenovirus formulation further comprises a salt selected from the group consisting of $MgCl_2$, $MnCl_2$, $CaCl_2$, $ZnCl_2$, NaCl and KCl.

In one embodiment, lyophilizing the adenovirus formulation is carried out in the presence of an inert gas.

In certain embodiments, the method for preparing the freeze dried adenovirus formulation, wherein lyophilizing the solution comprises the steps of, freezing the solution, subjecting the solution to a vacuum and subjecting the solution to at least a first and a second drying cycle, whereby the second drying cycle reduces the residual moisture content of the freeze-dried cake to less than about 2%.

In another embodiment, a method for the preparation of a long-term storage, stable adenovirus liquid formulation, comprising the steps of providing adenovirus and combining the adenovirus with a solution comprising a buffer and a polyol, whereby the adenovirus liquid formulation retains high infectivity.

Other objects, features and advantages of the present invention will become apparent from the following detailed description. It should be understood however, that the detailed description and the specific examples, while indicating preferred embodiments of the invention, are given by way of illustration only, since various modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
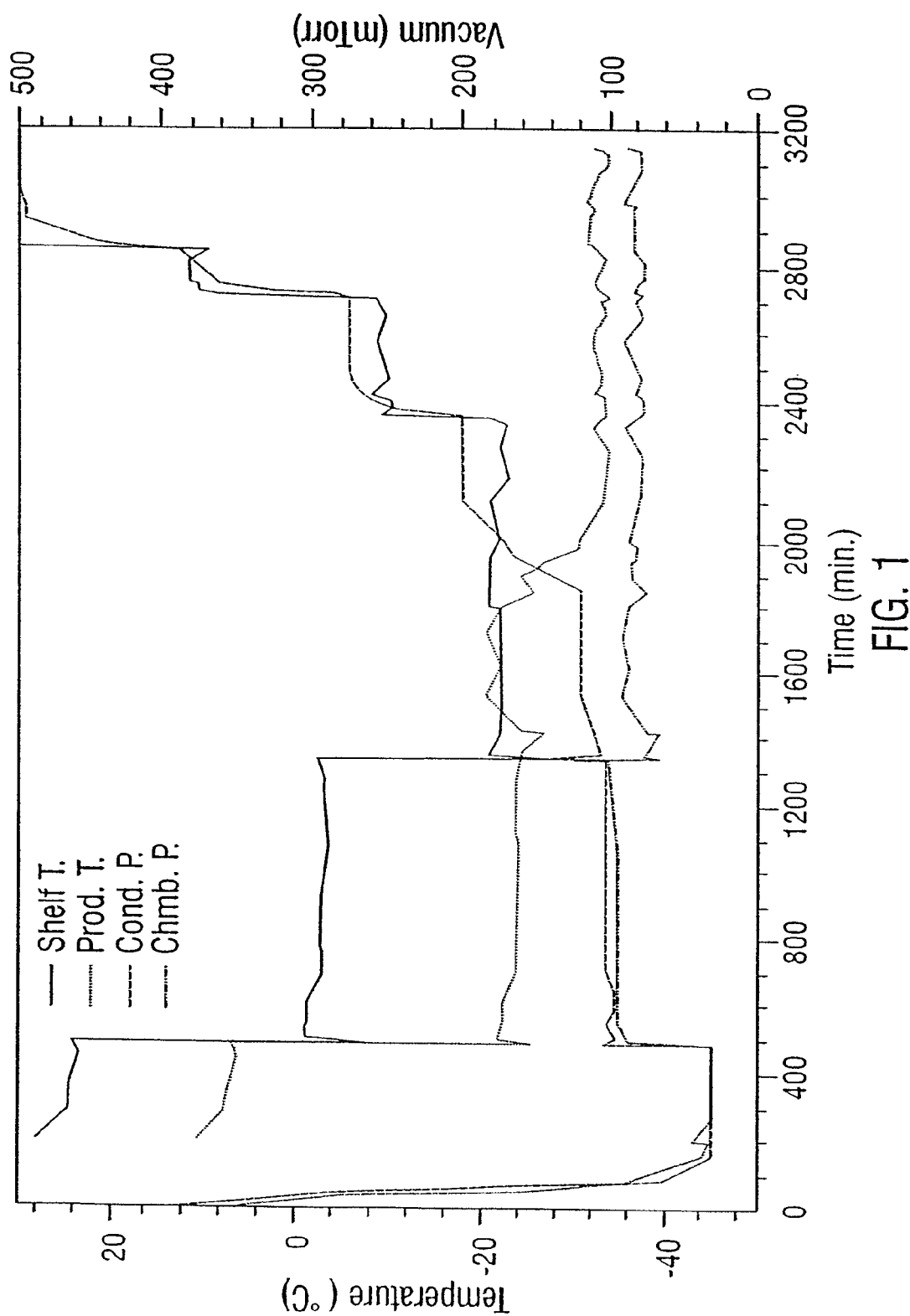
FIG. 1. Lyophilization Cycle of Adenovirus.
Figure 2:
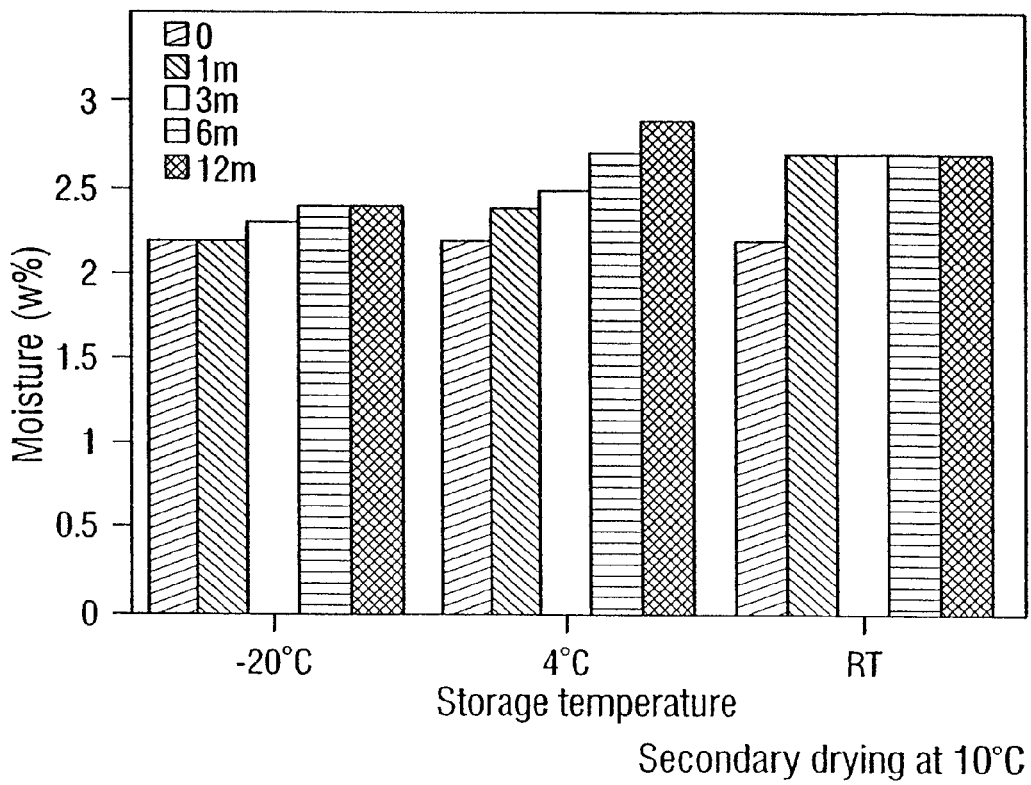
FIG. 2. Residual Moisture of Lyophilized Adenovirus After Secondary Drying at 10° C., FIG. 3. Stability of Lyophilized Adenovirus after Secondary Drying at 110° C.
Figure 3:
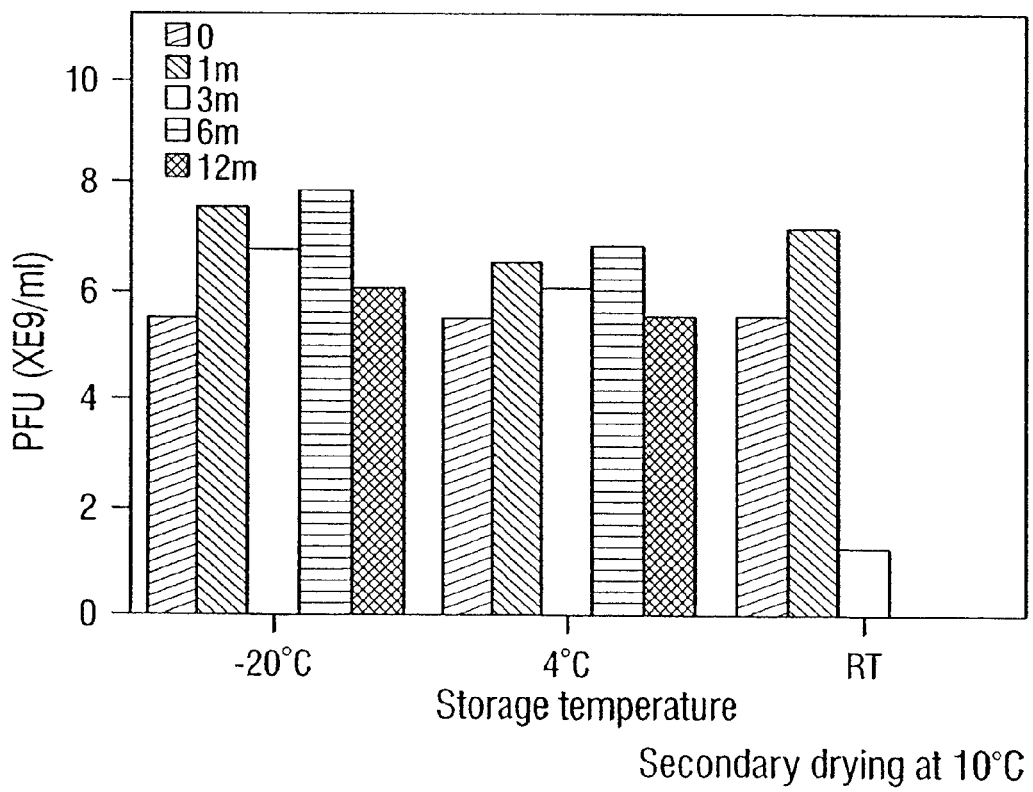
Figure 4:
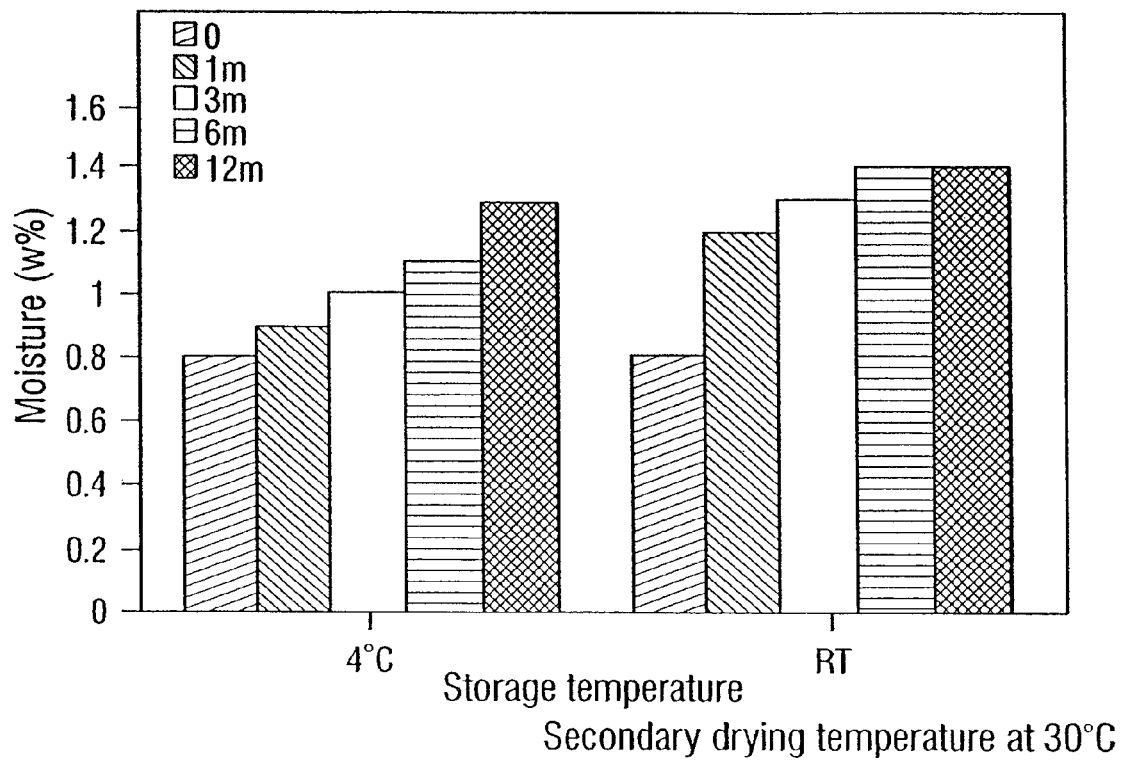
FIG. 4. Residual Moisture of Lyophilized Adenovirus After Secondary Drying at 30° C.
Figure 5:
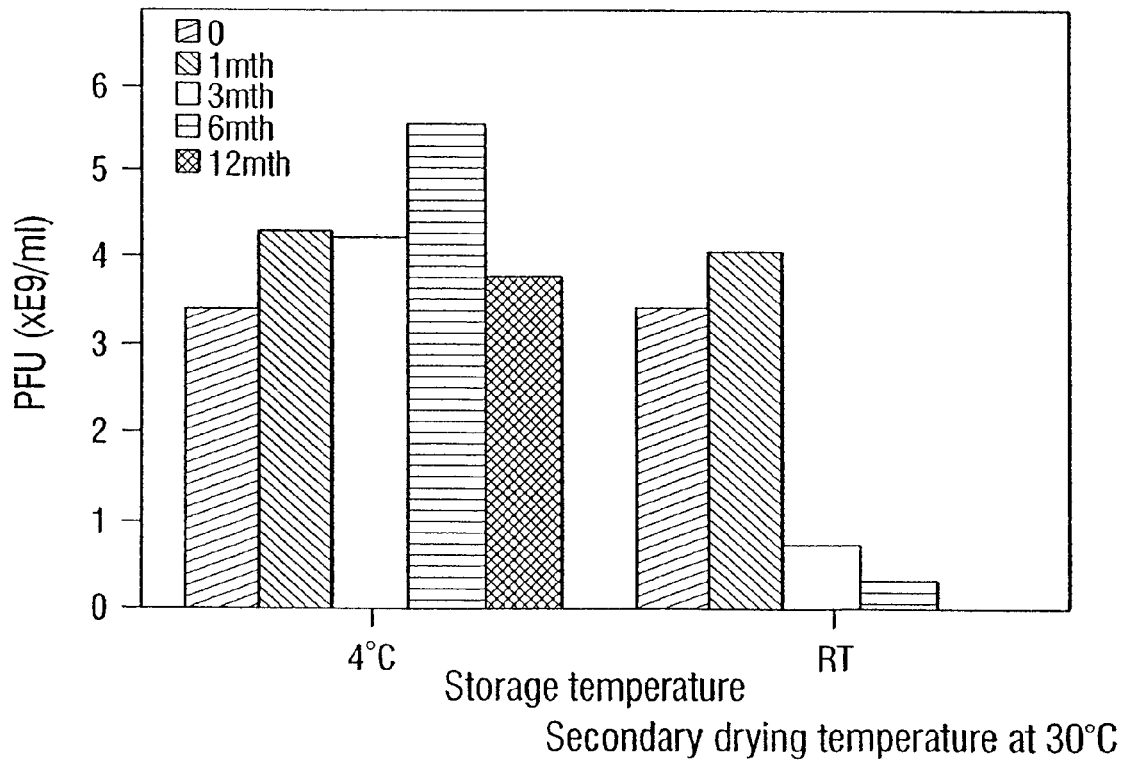
FIG. 5. Stability of Lyophilized Adenovirus after Secondary Drying at 30° C.
Figure 6:
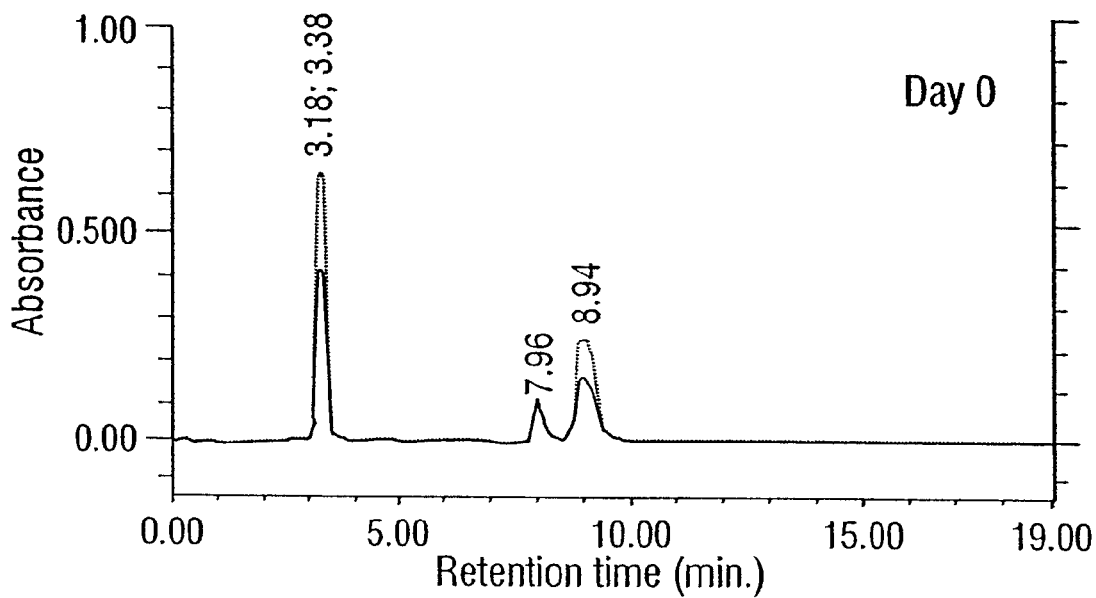
FIG. 6. HPLC Analysis of Lyophilized Adenovirus Stored at Room Temperature.
Figure 6:
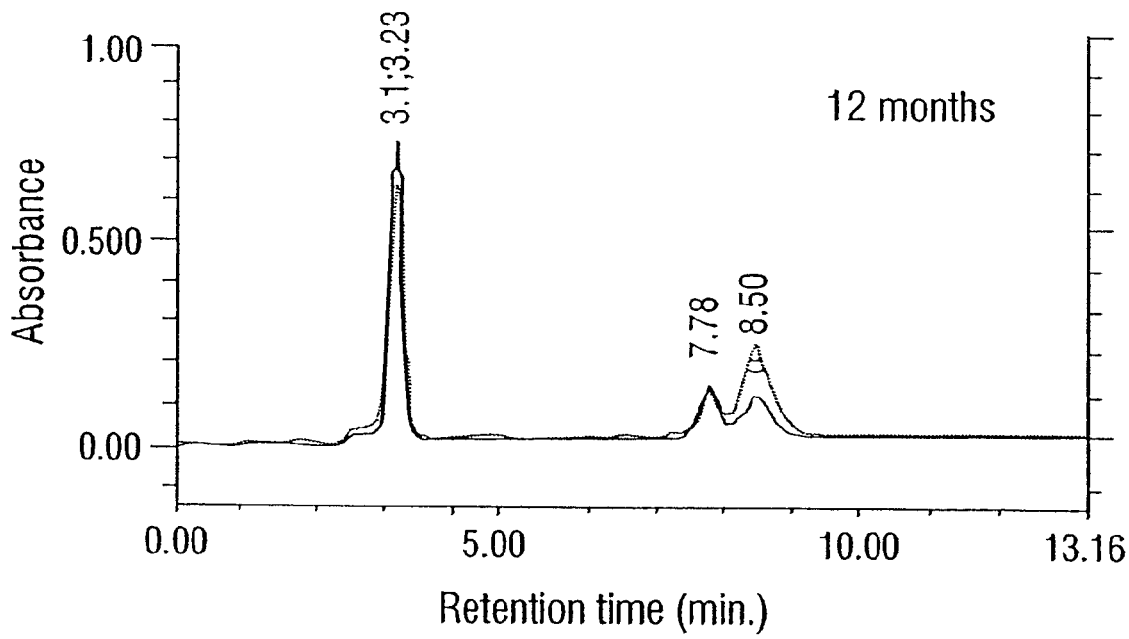
Figure 7:
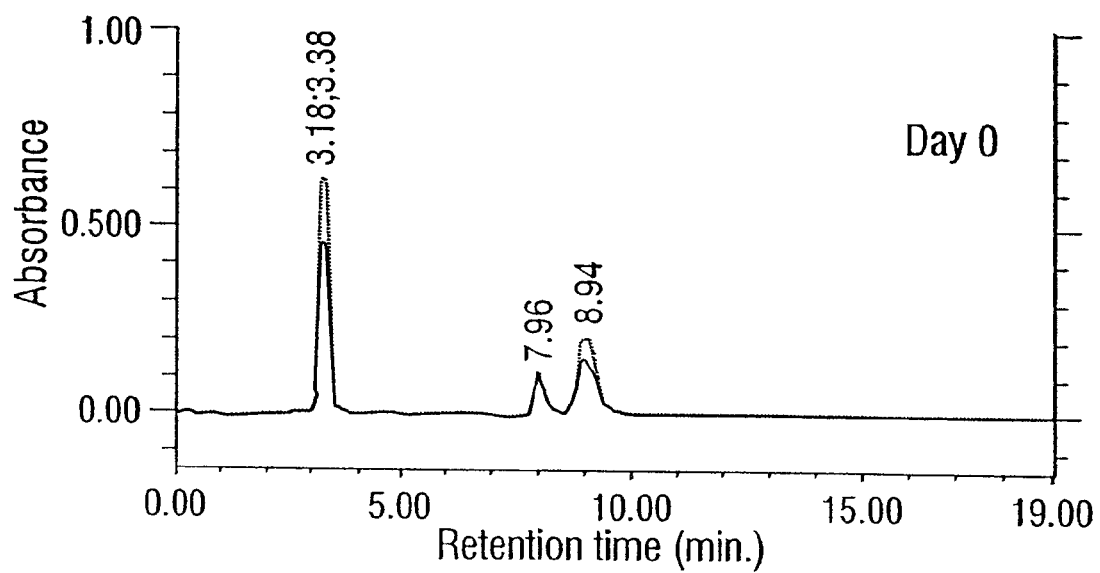
FIG. 7. HPLC Analysis of Lyophilized Adenovirus Stored at 4° C.
Figure 7:
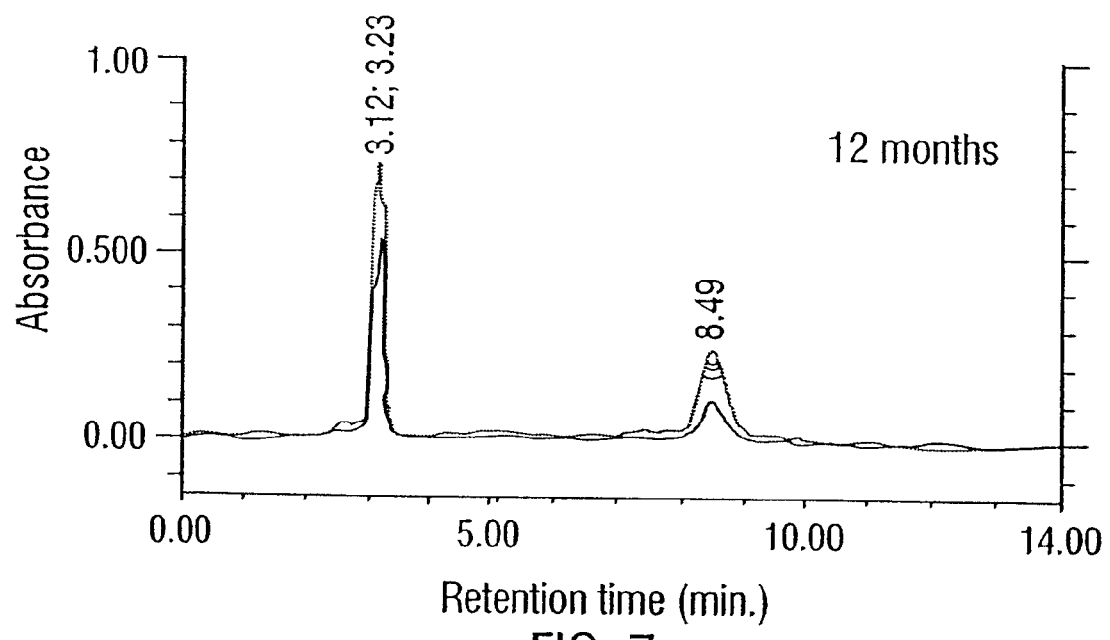
Figure 8:
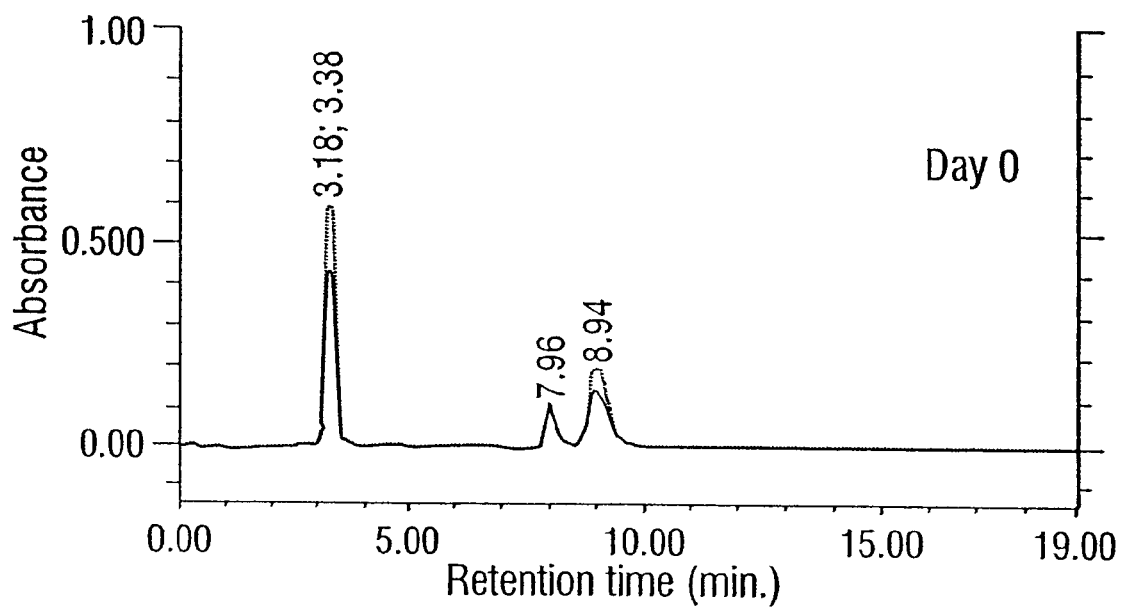
FIG. 8. HPLC Analysis of Lyophilized Adenovirus Stored at −20° C.
Figure 8:
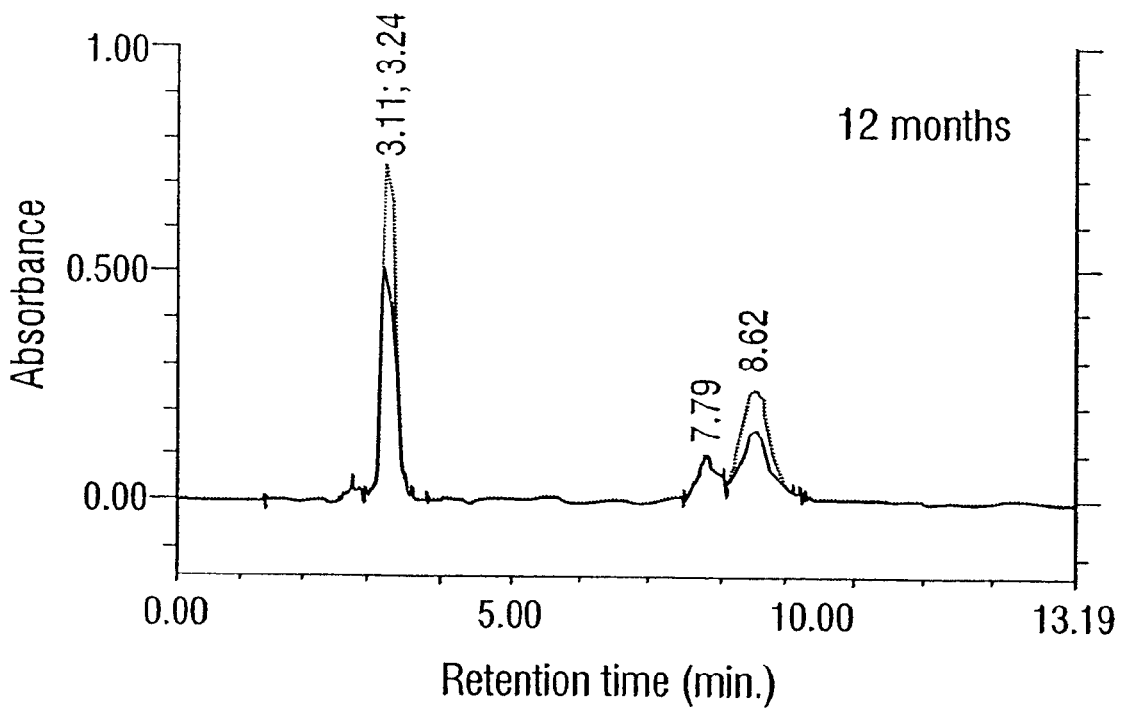
Figure 9A:
FIG. 9A and FIG. 9B. Addition of DMSO to the formulation for an adenoviral vector increases the transduction efficiency. Human NSCLC xenografts were established on the flanks of nude mice. Animals received intratumoral injection of $2 \times 10^{10}$ viral particles (vp) of Ad-βgal formulated in either PBS+glycerol (FIG. 9A and FIG. 9B, top panels) or in PBS+glycerol+5% DMSO (FIG. 9A and FIG. 9B, lower panels). Tumors were excised at either 24 (FIG. 9A) or 48 hours (FIG. 9L post-injection and sectioned for histochemical analysis of reporter gene expression. Histochemical analysis was done on multiple sections from the tumor block to analyze vector transduction and distribution. Two sections for each formulation are illustrated: one from the tumor periphery (FIG. 9A and FIG. 9B, left panels) and one from the center of the tumor (FIG. 9A and FIG. 9B, right panels). In each section both transduction (as indicated by intensity of blue staining) and distribution (as indicated by extent of blue staining) were improved by addition of DMSO to the formulation.
Figure 9A:
Figure 9A:
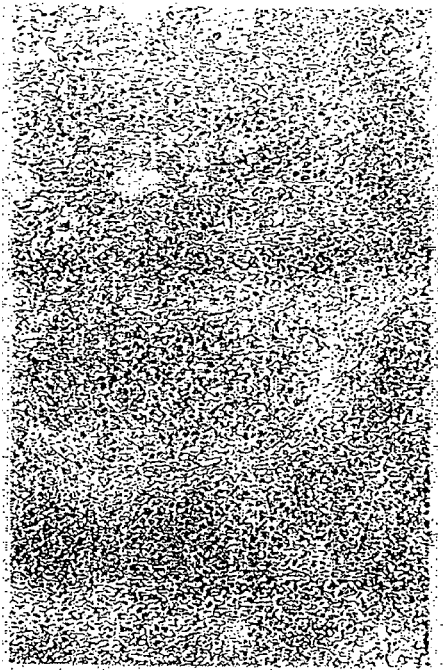
Figure 9A:
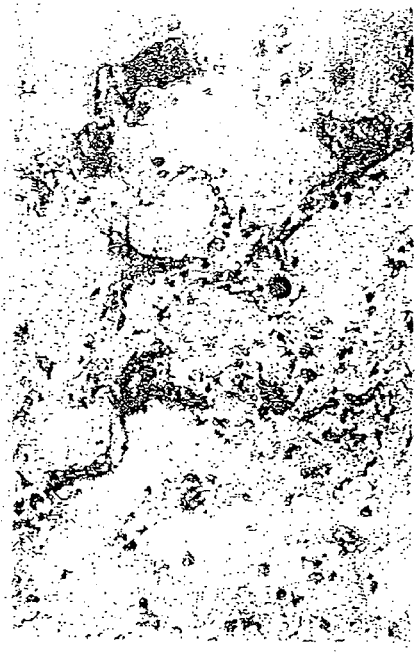
Figure 9B:
Figure 9B:
Figure 9B:
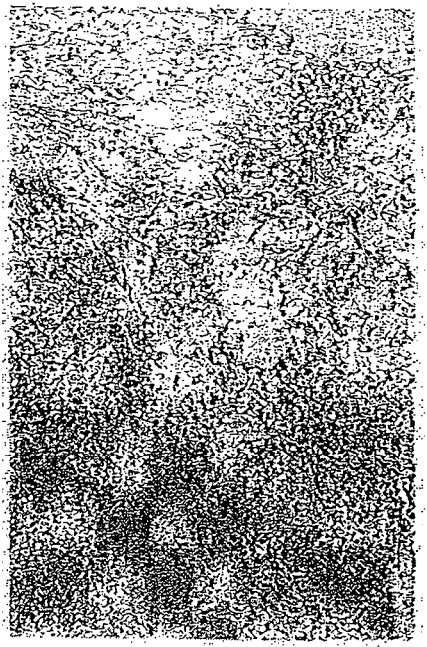
Figure 9B:

The need for long-term stable virus formulations that can be stored at or above refrigerated temperatures without losing infectivity is highly desirable. Traditional methods of ultra-low temperature storage ($\leq 60°$ C.) of virus preparations often limit the storage, transportation and clinical applications of viruses. The inventors have developed optimal lyophilization formulations for freeze-drying adenovirus in which the freeze-dried products maintain their stability (i.e., infectivity of 60-100% of the starting infectivity) and have a residual moisture of less than about 5% when stored for 6 months at 4° C.

In another embodiment, the inventors have developed long-term stable adenovirus formulations for storing adenovirus at 4° C. in a liquid form that maintains stability (i.e., infectivity of 60-100% of the starting infectivity) for at least 6 months.

A. PURIFICATION TECHNIQUES

A large scale process for the production and purification of adenovirus is described in U.S. Ser. No. 08/975,519 filed Nov. 20, 1997 (specifically incorporated herein by reference without disclaimer). This production process offers not only scalability and validatability but also virus purity comparable to that achieved using CsCl gradient ultracentrifugation. This process involves the preparation of recombinant adenovirus particles, the process comprising preparing a culture of producer cells by seeding producer cells into a culture medium, infecting cells in the culture after mid-log phase growth with a recombinant adenovirus comprising a selected recombinant gene operably linked to a promoter, harvesting recombinant adenovirus particles from the cell culture and removing contaminating nucleic acids. An important aspect of this process is the removal of contaminating nucleic acids using nucleases. Exemplary nucleases include Benzonase®, Pulmozyme®; or any other DNase or RNase commonly used within the art.

Enzymes such as Benzonaze® degrade nucleic acid and have no proteolytic activity. The ability of Benzonase® to rapidly hydrolyze nucleic acids makes the enzyme ideal for reducing cell lysate viscosity. It is well known that nucleic acids may adhere to cell derived particles such as viruses. The adhesion may interfere with separation due to agglomeration, change in size of the particle or change in particle charge, resulting in little if any product being recovered with a given purification scheme. Benzonase® is well suited for reducing the nucleic acid load during purification, thus eliminating the interference and improving yield.

As with all endonuclease, Benzonase® hydrolyzes internal phosphodiester bonds between specific nucleotides. Upon complete digestion, all free nucleic acids present in solution are reduced to oligonucleotides 2 to 4 bases in length.

The present invention further employs a number of different purification techniques to purify viral vectors of the present invention. Such techniques include those based on sedimentation and chromatography and are described in more detail herein below.

1. Density Gradient Centrifugation

There are two methods of density gradient centrifugation, the rate zonal technique and the isopycnic (equal density) technique, and both can be used when the quantitative separation of all the components of a mixture of particles is required. They are also used for the determination of buoyant densities and for the estimation of sedimentation coefficients.

Particle separation by the rate zonal technique is based upon differences in size or sedimentation rates. The technique involves carefully layering a sample solution on top of a performed liquid density gradient, the highest density of which exceeds that of the densest particles to be separated. The sample is then centrifuged until the desired degree of separation is effected, i.e., for sufficient time for the particles to travel through the gradient to form discrete zones or bands which are spaced according to the relative velocities of the particles. Since the technique is time dependent, centrifugation must be terminated before any of the separated zones pellet at the bottom of the tube. The method has been used for the separation of enzymes, hormones, RNA-DNA hybrids, ribosomal subunits, subcellular organelles, for the analysis of size distribution of samples of polysomes and for lipoprotein fractionations.

The sample is layered on top of a continuous density gradient which spans the whole range of the particle densities which are to be separated. The maximum density of the gradient, therefore, must always exceed the density of the most dense particle. During centrifugation, sedimentation of the particles occurs until the buoyant density of the particle and the density of the gradient are equal (i.e., where $p_p=p_m$ in equation 2.12). At this point no further sedimentation occurs, irrespective of how long centrifugation continues, because the particles are floating on a cushion of material that has a density greater than their own.

Isopycnic centrifugation, in contrast to the rate zonal technique, is an equilibrium method, the particles banding to form zones each at their own characteristic buoyant density. In cases where, perhaps, not all the components in a mixture of particles are required, a gradient range can be selected in which unwanted components of the mixture will sediment to the bottom of the centrifuge tube whilst the particles of interest sediment to their respective isopycnic positions. Such a technique involves a combination of both the rate zonal and isopycnic approaches.

Isopycnic centrifugation depends solely upon the buoyant density of the particle and not its shape or size and is independent of time. Hence soluble proteins, which have a very similar density (e.g., $p=1.3$ g $cm^{-3}$ in sucrose solution), cannot usually be separated by this method, whereas subcellular organelles (e.g., Golgi apparatus, $p=1.11$ g $cm^{-3}$, mitochondria, $p=1.19$ g $cm^{-3}$ and peroxisomes, $p=1.23$ g $cm^{-3}$ in sucrose solution) can be effectively separated.

As an alternative to layering the particle mixture to be separated onto a preformed gradient, the sample is initially mixed with the gradient medium to give a solution of uniform density, the gradient 'self-forming', by sedimentation equilibrium, during centrifugation. In this method (referred to as the equilibrium isodensity method), use is generally made of the salts of heavy metals (e.g., cesium or rubidium), sucrose, colloidal silica or Metrizamide.

The sample (e.g., DNA) is mixed homogeneously with, for example, a concentrated solution of cesium chloride. Centrifugation of the concentrated cesium chloride solution results in the sedimentation of the CsCl molecules to form a concentration gradient and hence a density gradient. The sample molecules (DNA), which were initially uniformly distributed throughout the tube now either rise or sediment until they reach a region where the solution density is equal to their own buoyant density, i.e. their isopycnic position, where they will band to form zones. This technique suffers from the disadvantage that often very long centrifugation times (e.g., 36 to 48 hours) are required to establish equilibrium. However, it is commonly used in analytical centrifugation to determine the buoyant density of a particle, the base composition of double stranded DNA and to separate linear from circular forms of DNA.

Many of the separations can be improved by increasing the density differences between the different forms of DNA by the incorporation of heavy isotopes (e.g., $^{15}N$) during biosynthesis, a technique used by Leselson and Stahl to elucidate the mechanism of DNA replication in *Esherichia coli*, or by the binding of heavy metal ions or dyes such as ethidium bromide. Isopycnic gradients have also been used to separate and purify viruses and analyze human plasma lipoproteins.

2. Chromatography

Purification techniques are well known to those of skill in the art. These techniques tend to involve the fractionation of the cellular milieu (e.g., density gradient centrifugation) to separate the adenovirus particles from other components of the mixture. Having separated adenoviral particles from the other components, the adenovirus may be purified using chromatographic and electrophoretic techniques to achieve complete purification. Analytical methods particularly suited to the preparation of a pure adenoviral particle of the present invention are ion-exchange chromatography, size exclusion chromatography and polyacrylamide gel electrophoresis. A particularly efficient purification method to be employed in conjunction with the present invention is HPLC.

Certain aspects of the present invention concern the purification, and in particular embodiments, the substantial purification, of an adenoviral particle. The term "purified" as used herein, is intended to refer to a composition, isolatable from other components, wherein the adenoviral particle is purified to any degree relative to its naturally-obtainable form. A purified adenoviral particle therefore also refers to an adenoviral component, free from the environment in which it may naturally occur.

Generally, "purified" will refer to an adenoviral particle that has been subjected to fractionation to remove various other components, and which composition substantially retains its expressed biological activity. Where the term "substantially purified" is used, this designation will refer to a composition in which the particle, protein or peptide forms the major component of the composition, such as constituting about 50% or more of the constituents in the composition.

Various methods for quantifying the degree of purification of a protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

There is no general requirement that the adenovirus, always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

Of course, it is understood that the chromatographic techniques and other purification techniques known to those of skill in the art may also be employed to purify proteins expressed by the adenoviral vectors of the present invention. Ion exchange chromatography and high performance liquid chromatography are exemplary purification techniques employed in the purification of adenoviral particles and are described in further detail herein below.

a. Ion-Exchange Chromatography

The basic principle of ion-exchange chromatography is that the affinity of a substance for the exchanger depends on both the electrical properties of the material and the relative affinity of other charged substances in the solvent. Hence, bound material can be eluted by changing the pH, thus altering the charge of the material, or by adding competing materials, of which salts are but one example. Because different substances have different electrical properties, the conditions for release vary with each bound molecular species. In general, to get good separation, the methods of choice are either continuous ionic strength gradient elution or stepwise elution. (A gradient of pH alone is not often used because it is difficult to set up a pH gradient without simultaneously increasing ionic strength.) For an anion exchanger, either pH and ionic strength are gradually increased or ionic strength alone is increased. For a cation exchanger, both pH and ionic strength are increased. The actual choice of the elution procedure is usually a result of trial and error and of considerations of stability. For example, for unstable materials, it is best to maintain fairly constant pH.

An ion exchanger is a solid that has chemically bound charged groups to which ions are electrostatically bound; it can exchange these ions for ions in aqueous solution. Ion exchangers can be used in column chromatography to separate molecules according to charge; actually other features of the molecule are usually important so that the chromatographic behavior is sensitive to the charge density, charge distribution, and the size of the molecule.

The principle of ion-exchange chromatography is that charged molecules adsorb to ion exchangers reversibly so that molecules can be bound or eluted by changing the ionic environment. Separation on ion exchangers is usually accomplished in two stages: first, the substances to be separated are bound to the exchanger, using conditions that give stable and tight binding; then the column is eluted with buffers of different pH, ionic strength, or composition and the components of the buffer compete with the bound material for the binding sites.

An ion exchanger is usually a three-dimensional network or matrix that contains covalently linked charged groups. If a group is negatively charged, it will exchange positive ions and is a cation exchanger. A typical group used in cation exchangers is the sulfonic group, $SO_3^-$. If an $H^+$ is bound to the group, the exchanger is said to be in the acid form; it can, for example, exchange on $H^+$ for one $Na^+$ or two $H^+$ for one $Ca^{2+}$. The sulfonic acid group is called a strongly acidic cation exchanger. Other commonly used groups are phenolic hydroxyl and carboxyl, both weakly acidic cation exchangers. If the charged group is positive—for example, a quaternary amino group—it is a strongly basic anion exchanger. The most common weakly basic anion exchangers are aromatic or aliphatic amino groups.

The matrix can be made of various material. Commonly used materials are dextran, cellulose, agarose and copolymers of styrene and vinylbenzene in which the divinylbenzene both cross-links the polystyrene strands and contains the charged groups. Table 1 gives the composition of many ion exchangers.

The total capacity of an ion exchanger measures its ability to take up exchangeable groups per milligram of dry weight. This number is supplied by the manufacturer and is important because, if the capacity is exceeded, ions will pass through the column without binding.

TABLE 1

| Matrix | Exchanger | Functional Group | Tradename |
|---|---|---|---|
| Dextran | Strong Cationic | Sulfopropyl | SP-Sephadex |
| | Weak Cationic | Carboxymethyl | CM-Sephadex |
| | Strong Anionic | Diethyl-(2-hydroxypropyl)-aminoethyl | QAE-Sephadex |
| | Weak Anionic | Diethylaminoethyl | DEAE-Sephadex |
| Cellulose | Cationic | Carboxymethyl | CM-Cellulose |
| | Cationic | Phospho | P-cel |
| | Anionic | Diethylaminoethyl | DEAE-cellulose |
| | Anionic | Polyethylenimine | PEI-Cellulose |
| | Anionic | Benzoylated-naphthoylated, deiethylaminoethyl | DEAE(BND)-cellulose |
| | Anionic | p-Aminobenzyl | PAB-cellulose |
| Styrene-divinyl-benzene | Strong Cationic | Sulfonic acid | AG 50 |
| | Strong Anionic | | AG 1 |
| | Strong Cationic + Strong Anionic | Sulfonic acid + Tetramethylammonium | AG 501 |
| Acrylic | Weak Cationic | Carboxylic | Bio-Rex 70 |
| Phenolic | Strong Cationic | Sulfonic acid | Bio-Rex 40 |
| Expoxyamine | Weak Anionic | Tertiary amino | AG-3 |

The available capacity is the capacity under particular experimental conditions (i.e., pH, ionic strength). For example, the extent to which an ion exchanger is charged depends on the pH (the effect of pH is smaller with strong ion exchangers). Another factor is ionic strength because small ions near the charged groups compete with the sample molecule for these groups. This competition is quite effective if the sample is a macromolecule because the higher diffusion coefficient of the small ion means a greater number of encounters. Clearly, as buffer concentration increases, competition becomes keener.

The porosity of the matrix is an important feature because the charged groups are both inside and outside the matrix and because the matrix also acts as a molecular sieve. Large molecules may be unable to penetrate the pores; so the capacity will decease with increasing molecular dimensions. The porosity of the polystyrene-based resins is determined by the amount of cross-linking by the divinylbenzene (porosity decreases with increasing amounts of divinylbenzene). With the Dowex and AG series, the percentage of divinylbenzene is indicated by a number after an X—hence, Dowex 50-X8 is 8% divinylbenzene Ion exchangers come in a variety of particle sizes, called mesh size. Finer mesh means an increased surface-to-volume ration and therefore increased capacity and decreased time for exchange to occur for a given volume of the exchanger. On the other hand, fine mesh means a slow flow rate, which can increase diffusional spreading. The use of very fine particles, approximately 10 µm in diameter and high pressure to maintain an adequate flow is called high-performance or high-pressure liquid chromatography or simply HPLC.

Such a collection of exchangers having such different properties—charge, capacity, porosity, mesh—makes the selection of the appropriate one for accomplishing a particular separation difficult. How to decide on the type of column material and the conditions for binding and elution is described in the following Examples.

There are a number of choice to be made when employing ion exchange chromatography as a technique. The first choice to be made is whether the exchanger is to be anionic or cationic. If the materials to be bound to the column have a single charge (i.e., either plus or minus), the choice is clear. However, many substances (e.g., proteins, viruses), carry both negative and positive charges and the net charge depends on the pH. In such cases, the primary factor is the stability of the substance at various pH values. Most proteins have a pH range of stability (i.e., in which they do not denature) in which they are either positively or negatively charged. Hence, if a protein is stable at pH values above the isoelectric point, an anion exchanger should be used; if stable at values below the isoelectric point, a cation exchanger is required.

The choice between strong and weak exchangers is also based on the effect of pH on charge and stability. For example, if a weakly ionized substance that requires very low or high pH for ionization is chromatographed, a strong ion exchanger is called for because it functions over the entire pH range. However, if the substance is labile, weak ion exchangers are preferable because strong exchangers are often capable of distorting a molecule so much that the molecule denatures. The pH at which the substance is stable must, of course, be matched to the narrow range of pH in which a particular weak exchanger is charged. Weak ion exchangers are also excellent for the separation of molecules with a high charge from those with a small charge, because the weakly charged ions usually fail to bind. Weak exchangers also show greater resolution of substances if charge differences are very small. If a macromolecule has a very strong charge, it may be impossible to elute from a strong exchanger and a weak exchanger again may be preferable. In general, weak exchangers are more useful than strong exchangers.

The Sephadex and Bio-gel exchangers offer a particular advantage for macromolecules that are unstable in low ionic strength. Because the cross-links in these materials maintain the insolubility of the matrix even if the matrix is highly polar, the density of ionizable groups can be made several times greater than is possible with cellulose ion exchangers. The increased charge density means increased affinity so that adsorption can be carried out at higher ionic strengths. On the other hand, these exchangers retain some of their molecular sieving properties so that sometimes molecular weight differences annul the distribution caused by the charge differences; the molecular sieving effect may also enhance the separation.

Small molecules are best separated on matrices with small pore size (high degree of cross-linking) because the available capacity is large, whereas macromolecules need large pore size. However, except for the Sephadex type, most ion exchangers do not afford the opportunity for matching the porosity with the molecular weight.

The cellulose ion exchangers have proved to be the best for purifying large molecules such as proteins and polynucleotides. This is because the matrix is fibrous, and hence all functional groups are on the surface and available to even the largest molecules. In may cases however, beaded forms such as DEAE-Sephacel and DEAE-Biogel P are more useful because there is a better flow rate and the molecular sieving effect aids in separation.

Selecting a mesh size is always difficult. Small mesh size improves resolution but decreases flow rate, which increases zone spreading and decreases resolution. Hence, the appropriate mesh size is usually determined empirically.

Because buffers themselves consist of ions, they can also exchange, and the pH equilibrium can be affected. To avoid these problems, the rule of buffers is adopted: use cationic buffers with anion exchangers and anionic buffers with cation exchangers. Because ionic strength is a factor in binding, a buffer should be chosen that has a high buffering capacity so that its ionic strength need not be too high. Furthermore, for best resolution, it has been generally found that the ionic conditions used to apply the sample to the column (the so-called starting conditions) should be near those used for eluting the column.

b. High Performance Liquid Chromatography

High performance liquid chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

B. VIRAL FORMULATION

Retrovirus, adenovirus, adeno-associated virus, and herpes simplex virus are the most commonly used viruses in gene therapy (Robbins and Ghivizzani; 1998). It is contemplated in the present invention that the preparation of long-term stable adenovirus vectors that can be stored at or above refrigerated temperatures would be useful as gene therapy vectors. Viral particles must maintain their structural integrity to remain infective and biologically active for use as gene therapy vectors. Current virus formulations do not readily make it feasible to store or transport viral vector at or above refrigerated temperatures without significant loss of viral infectivity.

The present invention describes long-term stable adenovirus formulations that can be stored at 4° C. for periods up to 6 months. In one embodiment of the present invention, adenovirus preparations are formulated for lyophilization and long-term storage at 4° C. as freeze-dried adenovirus. In another embodiment, the adenovirus is prepared as a liquid formulation that is long-term stable at 4° C. An important aspect of both the lyophilized and liquid adenovirus formulations is the addition of at least one or more compounds that improve the long-term, storage stability of the adenovirus.

The term "compound" in the context of the present invention includes pharmaceutically acceptable carriers such as bulking agents, cryoprotectants, lyoprotectants, preservatives, solvents, solutes and any additional pharmaceutical agents well known in the art. Buffering agents and other types of pH control can also be added simultaneously in order to provide for maximum buffering capacity for the adenovirus formulation. For example, pH changes that deviate from physiological conditions often result in irreversible aggregation of proteins (Wetzel, 1992) and viral capsids (Misselwitz et al., 1995) due to complete or partial denaturation of the protein. Thus, buffering agents are particularly important for virus preparations that aggregate or denature at sub-optimal pH ranges.

1. Lyophilized Formulations

The formulation of lyophilized, long-term storage stable adenovirus in the present invention requires the presence of one or more excipients. More particularly, for optimal long-term stability of lyophilized adenovirus formulations, a bulking agent and one or more protectants are desirable. It is well known in the art that loss in virus infectivity often is directly related to denaturation, self association and aggregation of the viral particles (Misselwitz et al., 1995; Vanlandschoot et al., 1998; Sagrera et al., 1998; Lu et al., 1998). In fact, the *E. coli* heat shock proteins GroEL/GroES have been shown to both stabilize viral particles from denaturation and aggregation during high stress cellular conditions and to facilitate capsid assembly during non-stressed, normal cellular conditions (Polissi et al., 1995; Nakonechny and Teschke, 1998).

The use of bulking agents, cryoprotectants, lyoprotectants and salts in the present invention are included in the formulation of lyophilized adenovirus to improve long-term stability (i.e. infectivity) of the adenovirus freeze-dried products. The stabilizing effect of the cryoprotectant sucrose against irreversible denaturation and aggregation has been described previously as an excluded volume effect (Hall et al., 1995). Similarly, bulking agents, cryo- and lyoprotectants such as polyacrylamide gels, agaorse gels, dextran and polyethylene glycol (PEG) have demonstrated enhanced stabilities of proteins and nucleic acids in part by excluded volume effects (Fried and Bromberg, 1997; Vossen and Fried, 1997). The exact mechanistic details of excluded volume effects are still not clear. A currently accepted theory is that many of these compounds result in the preferential hydration of protein molecules (i.e. volume of exclusion), which tends to stabilize the native versus the denatured conformation of proteins, and therefore prevents aggregation. In addition, the presence of low concentrations of cosolvents (e.g., salts) result in charge screening of proteins and viral protein coats increasing their solubility in water.

The use of bulking agents, cryoprotectants, lyoprotectants and salts in the present invention are contemplated and demonstrated experimentally to improve the storage stability of lyophilized adenovirus products. In one embodiment, a bulking agent and protectants are combined with a buffer comprising adenovirus.

Bulking agents, cryoprotectants and lyoprotectants are well known in the art (Lueckel et al., 1998; Herman et al., 1994; Croyle et al., 1998; Corveleyn and Remon, 1996). Bulking agents considered in the present invention are mannitol, inositol, lactitol, xylitol, isomaltol, sorbitol, gelatin, agar, pectin, casein, dried skim milk, dried whole milk, silcate, carboxypolymethylene, hydroxyethyl cellulose, hydroxypropyl cellulose, hydroxypropyl methhylcellulose, methylcellulose and other bulking agents well known in the art. Cryoprotectants considered are sucrose, dextrose, lactose, trehalose, glucose, maltose, niacinamide, creatinine, monosodium glutamate, dimethyl sulfoxide, sweet whey solids, as well as other known cryoprotectants. Lyoprotectants contemplated for use in the present invention are human serum albumin, bovine serum albumin, PEG, glycine, arginine, proline, lysine, alanine, polyvinyl pyrrolidine, polyvinyl alcohol, polydextran, maltodextrins, hydroxypropyl-beta-cyclodextrin, partially hydrolysed starches, Tween-20 and Tween-80. Certain lyoprotectants are also classified as cryoprotectants and vice versa. For the purpose of the present invention, cryoprotectants and lyoprotectants are represented as independent classes of compounds. However, this classification is only for clarity of the invention and should not limit the person skilled in the art from using any excipient that stabilizes the adenovirus formulation. In other embodiments of the present invention, the term excipient encompasses bulking agents, cryo- and lyoprotectants. In certain embodiments, salts are included in the formulation in addition to the aforementioned excipients. The following salts are considered for use in the present invention $MgCl_2$, $MnCl_2$, $CaCl_2$, $ZnCl_2$, NaCl, and KCl, but should not preclude the use of other salts that improve stability of the adenovirus formulation.

In other embodiments of the invention, the lyophilized adenovirus formulation is dried in the presence of an inert gas or a combination of inert gasses. The purging of the lyophilization vessel with an inert gas or gasses, the presence of the inert gas or gasses during lyophilization of the adenovirus solution and during the capping of the lyophilization vial after the drying step, are contemplated to minimize the deleterious effects of $O_2$. It is known that residual $O_2$ leads to oxidation and degradation of proteins. It is contemplated that purging and capping of the freeze-dried adenovirus product improves the long-term storage stability of the adenovirus product. The use of antioxidants such as β-mercapto ethanol, DTT, citric acid and the like may also be considered for use in formulations.

An important aspect of the lyophilization process is a second drying cycle. The second drying cycle is at a temperature of 30° C. for at least 3.5 hours, which is demonstrated to reduce the residual moisture of the adenovirus freeze-dried product to less than 2% water immediately after drying. It is contemplated that the reduced residual moisture improves the long-term storage stability of the adenovirus freeze-dried product. Longer drying times up to 20 hours are thus contemplated to further reduce residual moisture.

2. Liquid Formulations

The formulation of liquid, long-term storage stable adenovirus in the present invention requires the presence of a polyol. A polyol is a polyhydric alcohol containing two or more hydroxyl groups. For optimal long-term stability of liquid adenovirus formulations in the present invention, glycerol is used. In particular embodiments of the invention, the presence 20% glycerol results in adenovirus stability (80% PFU/mL) for periods of time at least up to 6 months days when stored at 4° C.

Glycerol (glycerin) is one of the oldest and most widely used excipients in pharmaceutical products. It is a clear, colorless liquid which is miscible with water and alcohol. Glycerol is hygroscopic, stable to mild acidic and basic environments and can be sterilized at temperatures up to 150° C. It is well known as both a taste masking and cryoprotective agent, as well as an antimicrobial agent. It has good solubilizing power and is a commonly used solvent in parenteral formulations. It is considered to be one of the safest excipients used since it is metabolized to glucose, or to substances which are involved with triglyceride synthesis or glycolysis (Frank et al., 1981). It is a GRAS listed excipient and typically used at levels up to 50% in parenteral formulations.

The stabilizing effects of glycerol on protein structure is well known in the art (Hase et al., 1998; Juranville et al., 1998). Several studies indicate that glycerol has a similar effect of viral particles. For example, when competent *Haemophilus influenza* bacteria were exposed to purified phage and plated for transfectants, a 100-fold increase in transfectants was observed when 32% glycerol was present in the solution (Stuy, 1986) In yet another study, glycerol was demonstrated to preserve the integrity of vaccinia virus (Slonin and Roslerova, 1969).

Other polyols contemplated for use in the present invention are polyethylene glycol, propylene glycol, sorbitol, mannitol, and the like. Polyethylene glycols are polymers of ethylene oxide with the general formula:

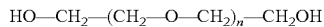

where n represents the number of oxyethylene groups. The PEG's are designated by a numerical value, which is indicative of the average molecular weight for a given grade. Molecular weights below 600 are liquids, and molecular weights above 1000 are solids at room temperature. These polymers are readily soluble in water, which make them quite useful for parenteral dosage forms. Only PEG 400 and PEG 300 are utilized in parenteral products, typically at concentrations up to 30% v/v. These polymers are generally regarded as non-toxic and non-irritating. There are numerous reviews regarding the pharmaceutical and toxicological characteristics of these polyols (Smyth et al., 1950; Rowe and Wolf, 1982, Swarbrick and Boylan, 1990).

Propylene glycol, a dihydroxy alcohol, is one of the more common solvents encountered in pharmaceutical cosolvent formulations, for both parenteral and non-parenteral dosage forms. PG is generally regarded as non-toxic. It is more hygroscopic than glycerin, and has excellent solubilizing power for a wide variety of compounds. In addition, it has excellent bacteriocidal and preservative properties (Heine et al., 1950). PG is metabolized to carbon dioxide and water via lactic and pyruvic acid intermediates and, therefore, not prone to the severe toxicities.

Sorbitol and mannitol are hexahydric alcohols, consisting of white, crystalline powders, that are soluble in water. Both are commonly used excipients in pharmaceutical products with little or no toxicity associated, as approved by the FDA for food use. The mechanistics of sorbitol and mannitol protein and viral stabilization is still not completely understood. Current theories suggest at least part of the effect is osmotic diuretic (Vanholder, et al., 1984; de Rizzo, et al., 1988). The use of the polyols described above are considered exemplary, but should not limit the skilled artist from selecting other polyols that confer viral stability for liquid formulations.

It is also contemplated, in addition to a polyol in the liquid formulation, that one or possibly two excipients may also be included. Excipients considered for use in the present invention are inositol, lactitol, xylitol, isomaltol, gelatin, agar, pectin, casein, dried skim milk, dried whole milk, silcate, carboxypolymethylene, hydroxyethyl cellulose, hydroxypropyl cellulose, hydroxypropyl methhylcellulose, methylcellulose, sucrose, dextrose, lactose, trehalose, glucose, maltose, niacinamide, creatinine, monosodium glutamate, dimethyl sulfoxide, sweet whey solids, human serum albumin, bovine serum albumin, glycine, arginine, proline, lysine, alanine, polyvinyl pyrrolidine, polyvinyl alcohol, polydextran, maltodextrins, hydroxypropyl-beta-cyclodextrin, partially hydrolysed starches, Tween-20 and Tween-80. The choice of a particular excipient is dependent in some instances on the desired properties of the viral formulation.

In particular embodiments, dimethyl sulfoxide (DMSO) is contemplated for use in the present invention. DMSO has been demonstrated to enhance the infectivity of adenovirus preparations by increasing the efficiency of gene transfer (Chikada and Jones, 1999). For example, the infectivity of adenovirus type 2 DNA in 293 cells was increased up to five-fold by the brief treatment of cell monolayers with 25% DMSO (Chinnadurai et al., 1978) The stabilization of virus particles via DMSO also has been reported (Wallis and Melnick, 1968). The present inventors demonstrate that the intratumoral administration of Ad-p53 is improved when DMSO is added to 5 or 10% (see FIG. 9). Adenovirus studies via intravesical administration indicate that an adenoviral vector may be stable in up to 50% DMSO (WO 98/35554). In other embodiments, a polyol contemplated for use in the present invention as an enhancer of adenovirus gene transduction is a polyoxyalkene (U.S. Pat. No. 5,552,309, specifically incorporate herein by reference in its entirety).

Thus in particular embodiments, an adenoviral formulation according to the present invention may also contain DMSO. The concentration for intratumoral administration may contain from about 2% to 67% DMSO, preferably from about 5% to 20%. The concentration for intravesical administration may contain from about 2% to 67% DMSO, preferably from about 20% to 50%. The concentration for topical administration may contain from about 2% to 67% DMSO, preferably from about 10% to 40%. The concentration for intra-articular administration may contain from about 2% to 67% DMSO, preferably, from about 5% to 40%. The concentration for systemic administration may contain from about 2% to 75% DMSO, preferably from about 50% to 67%.

Adenovirus polyol formulations of the invention may future comprise a polyoxamer, such as Polyoxamer 407, at concentrations of from about 0.5% to 20%, preferably from about 10% to 20%. The formulation storage stable adenovirus may also contain from about 5% to 40% dimethylacetamide, preferably from about 10% to 25%, Or it may contain from about 10% to 50% of a polyethylene glycol, such as polyethylene glycol 400, preferably from about 15% to 50%. Of course, the formulation of said adenovirus also may contain combinations of the above components.

C. VIRAL TRANSFORMATION

The present invention employs, in one example, adenoviral infection of cells in order to generate therapeutically significant vectors. Typically, the virus will simply be exposed to the appropriate host cell under physiologic conditions, permitting uptake of the virus. Though adenovirus is exemplified, the present methods may be advantageously employed with other viral vectors, as discussed below.

1. Viral Infection a. Adenovirus

One method for delivery of the recombinant DNA involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a)

support packaging of the construct and (b) to ultimately express a recombinant gene construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) have disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Adenoviral vectors also have been described for treatment of certain types of cancers (U.S. Pat. No. 5,789,244, specifically incorporated herein by reference in its entirety). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

b. Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

c. Adeno-Associated Virus

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994a; Clark et al., 1995). Cell lines carrying the rAAV DNA as an integrated provirus can also be used (Flotte et al., 1995).

d. Other Viral Vectors

Other viral vectors may be employed as constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Also contemplated for use in the present invention is a fairly new class of viruses termed oncolytic virus (Pennisi, 1998). Some of the viruses included in this group are reovirus, the genetically modified adenovirus OYNX-015 and CN706. These oncolytic viruses, which have not been genetically altered to prevent their replication, destroy certain types of cancer cells by multiplying and spreading, killing only the cancer cells. Each of the above oncolytic viruses are proposed to operate via different pathways involved in cancers.

For example, human reovirus requires an activated Ras signaling pathway for infection of cultured cells. Thus, in certain tumors with an overactive ras gene, reovirus readily replicates. In a study on reovirus, severe combined immune deficient mice bearing tumors established from v-erbB-transformed murine NIH 3T3 cells or human U87 glioblastoma cells were treated with the virus. A single intratumoral injection of virus resulted in regression of tumors in 65% to 80% of the mice. Treatment of immune-competent C3H mice bearing tumors established from a ras-transformed C3H-10T1/2 cells also resulted in tumor regression, although a series of injections were required (Coffey et al., 1998)

2. Vectors and Regulatory Signals

Vectors of the present invention are designed, primarily, to transform cells with a gene under the control of regulated eukaryotic promoters (i.e., inducible, repressable, tissue specific). Also, the vectors usually will contain a selectable marker if, for no other reason, to facilitate their production in vitro. However, selectable markers may play an important role in producing recombinant cells and thus a discussion of promoters is useful here. Table 2 and Table 3 below, list inducible promoter elements and enhancer elements, respectively.

TABLE 2

Inducible Elements

| Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | poly(rI)X poly(rc) | Tavernier et al., 1983 |
| Adenovirus 5 E2 | Ela | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone α Gene | Thyroid Hormone | Chatterjee et al., 1989 |

TABLE 3

Other Promoter/Enhancer Elements

| Promoter/Enhancer | References |
|---|---|
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |

TABLE 3-continued

Other Promoter/Enhancer Elements

| Promoter/Enhancer | References |
| --- | --- |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_{1-Antitrypain}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

Another signal that may prove useful is a polyadenylation signal (hGH, BGH, SV40).

The use of internal ribosome binding sites (IRES) elements are used to create multigene, or polycistronic, messages. IRES elements are able to bypass the ribosome scanning model of 5'-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

As discussed above, in certain embodiments of the invention, a cell may be identified and selected in vitro or in vivo by including a marker in the expression construct. Such markers confer an identifiable change to the cell permitting easy identification of cells containing the expression construct. Usually, the inclusion of a drug selection marker aids in cloning and in the selection of transformants, for example, genes that confer resistance to neomycin, puromycin, hygromycin, DHFR, GPT, zeocin, tetracycline and histidinol are useful selectable markers. Alternatively, enzymes such as herpes simplex virus thymidine kinase (tk) or chloramphenicol acetyltransferase (CAT) may be employed.

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

In any event, it will be understood that promoters are DNA elements which when positioned functionally upstream of a gene leads to the expression of that gene. Most transgene constructs of the present invention are functionally positioned downstream of a promoter element.

D. ENGINEERING OF VIRAL VECTORS

In certain embodiments, the present invention further involves the manipulation of viral vectors. Such methods involve the use of a vector construct containing, for example, a heterologous DNA encoding a gene of interest and a means for its expression, replicating the vector in an appropriate helper cell, obtaining viral particles produced therefrom, and infecting cells with the recombinant virus particles. The gene could simply encode a protein for which large quantities of the protein are desired, i.e., large scale in vitro production methods. Alternatively, the gene could be a therapeutic gene, for example to treat cancer cells, to express immunomodulatory genes to fight viral infections, or to replace a gene's function as a result of a genetic defect. In the context of the gene therapy vector, the gene will be a heterologous DNA, meant to include DNA derived from a source other than the viral genome which provides the backbone of the vector. Finally, the virus may act as a live viral vaccine and express an antigen of interest for the production of antibodies they are against. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA may also include a regulatory sequence which may be derived from one source and the gene from a different source.

1. Therapeutic Genes p53 currently is recognized as a tumor suppressor gene (Montenarh, 1992). High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers (Mercer, 1992). It is mutated in over 50% of human NSCLC (Hollestein et al., 1991) and in a wide spectrum of other tumors.

The p53 gene encodes a 393-amino-acid phosphoprotein that can form complexes with host proteins such as large-T antigen and E1B. The protein is found in normal tissues and cells, but at concentrations which are generally minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus; p53 can act as a negative regulator of cell growth (Weinberg, 1991) and may directly suppress uncontrolled cell growth or directly or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 is not detrimental to normal cells with endogenous wild-type p53. Thus, such constructs might be taken up by normal cells without adverse effects. It is thus proposed that the treatment of p53-associated cancers with wild-type p53 expression constructs will reduce the number of malignant cells or their growth rate. Furthermore, recent studies suggest that some p53 wild-type tumors are also sensitive to the effects of exogenous p53 expression.

The major transitions of the eukaryotic cell cycle are triggered by cyclin-dependent kinases, or CDK's. One CDK, cyclin-dependent kinase 4 (CDK4), regulates progression through the $G_1$ phase. The activity of this enzyme may be to phosphorylate Rb at late $G_1$. The activity of CDK4 is controlled by an activating subunit, D-type cyclin, and by an inhibitory subunit, e.g. $p16^{INK4}$, which has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, $p2^{WAF1,CIP1,SD11}$ and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994a; Kamb et al., 1994b; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap 1995).

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993a; 1993b and 1993c) demonstrated that the first Ig domain of C-CAM is critical for cell adhesion activity.

Cell adhesion molecules, or CAMs are known to be involved in a complex network of molecular interactions that regulate organ development and cell differentiation (Edelman, 1985). Recent data indicate that aberrant expression of CAMs may be involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. CAM now has been shown to suppress tumor growth in vitro and in vivo.

Other tumor suppressors that may be employed according to the present invention include RB, APC, DCC, NF-1, NF-2, WT-1, MEN-I, MEN-II, zac1, p73, BRCA1, VHL, FCC, MMAC1, MCC, p16, p21, p57, C-CAM, p27 and BRCA2. Inducers of apoptosis, such as Bax, Bak, Bcl-$X_s$, Bik, Bid, Harakiri, Ad E1B, Bad and ICE-CED3 proteases, similarly could find use according to the present invention.

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

Hormones are another group of gene that may be used in the vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1-40), parathyroid hormone-related protein (107-139) (PTH-rP), parathyroid hormone-related protein (107-111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, alpha melanocyte stimulating hormone (alpha-MSH), atrial natriuretic factor (5-28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH).

Other classes of genes that are contemplated to be inserted into the vectors of the present invention include interleukins and cytokines. Interleukin 1 (IL-1), IL-2, IL-3, IL-4, IL-5, IL-6, IL-7, IL-8, IL-9, IL-10, IL-11 IL-12, GM-CSF and G-CSF.

Examples of diseases for which the present viral vector would be useful include, but are not limited to, adenosine deaminase deficiency, human blood clotting factor IX deficiency in hemophilia B, and cystic fibrosis, which would involve the replacement of the cystic fibrosis transmembrane receptor gene. The vectors embodied in the present invention could also be used for treatment of hyperproliferative disorders such as rheumatoid arthritis or restenosis by transfer of genes encoding angiogenesis inhibitors or cell cycle inhibitors. Transfer of prodrug activators such as the HSV-TK gene can be also be used in the treatment of hyperploiferative disorders, including cancer.

2. Antisense Constructs

Oncogenes such as ras, myc, neu, raf erb, src, fms, jun, trk, ret, gsp, hst, bcl and abl also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementarity rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" refers to an RNA-based enzyme capable of targeting and cleaving particular base sequences in oncogene DNA and RNA. Ribozymes can either be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

3. Antigens for Vaccines

Other therapeutics genes might include genes encoding antigens such as viral antigens, bacterial antigens, fungal antigens or parasitic antigens. Viruses include picornavirus, coronavirus, togavirus, flavirviru, rhabdovirus, paramyxovirus, orthomyxovirus, bunyavirus, arenvirus, reovirus, retrovirus, papovavirus, parvovirus, herpesvirus, poxvirus, hepadnavirus, and spongiform virus. Preferred viral targets include influenza, herpes simplex virus 1 and 2, measles, small pox, polio or HIV. Pathogens include trypanosomes, tapeworms, roundworms, helminths. Also, tumor markers, such as fetal antigen or prostate specific antigen, may be targeted in this manner. Preferred examples include HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. Preferably, vaccination of an individual would only be required infrequently, such as yearly or biennially, and provide long term immunologic protection against the infectious agent.

4. Control Regions

In order for the viral vector to effect expression of a transcript encoding a therapeutic gene, the polynucleotide encoding the therapeutic gene will be under the transcriptional control of a promoter and a polyadenylation signal. A "promoter" refers to a DNA sequence recognized by the synthetic machinery of the host cell, or introduced synthetic machinery, that is required to initiate the specific transcription of a gene. A polyadenylation signal refers to a DNA sequence recognized by the synthetic machinery of the host cell, or introduced synthetic machinery, that is required to direct the addition of a series of nucleotides on the end of the mRNA transcript for proper processing and trafficking of the transcript out of the nucleus into the cytoplasm for translation. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work; have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

E. PHARMACEUTICAL COMPOSITIONS

In certain embodiments, the present invention also concerns formulations of a viral composition for administration to a mammal. It will also be understood that, if desired, the viral compositions disclosed herein may be administered in combination with other agents as well, such as, e.g., various pharmaceutically-active agents. As long as the compositions do not cause a significant adverse effect upon contact with the target cells or host tissues, there is virtually no limit to other components which may also be included.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

1. Injectable Compositions and Delivery

The pharmaceutical compositions disclosed herein may be administered parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

2. Oral Compositions and Delivery

Alternatively, the pharmaceutical compositions disclosed herein may be delivered via oral administration to an animal, and as such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as those containing sodium borate, glycerin and potassium bicarbonate, or dispersed in a dentifrice, including: gels, pastes, powders and slurries, or added in a therapeutically effective amount to a paste dentifrice that may include water, binders, abrasives, flavoring agents, foaming agents, and humectants, or alternatively fashioned into a tablet or solution form that may be placed under the tongue or otherwise dissolved in the mouth.

3. Nasal Delivery

The administration of agonist pharmaceutical compositions by intranasal sprays, inhalation, and/or other aerosol delivery vehicles is also considered. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety), and delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Lyophilizer

A Dura-stop µp lyophilizer (FTSsystems) with in process sample retrieving device was used. The lyophilizer is equipped with both thermocouple vacuum gauge and capacitance manometer for vacuum measurement. Condenser temperature is programmed to reach to −80° C. Vials were stoppered at the end of each run with a build-in mechanical stoppering device.

Residual Moisture Measurement

Residual moisture in freeze dried product was analyzed by a Karl-Fisher type coulometer (Mettler DL37, KF coulometer).

HPLC Analysis

HPLC analysis of samples was done on a Beckman Gold HPLC system.

Vials and Stoppers

Borosilicate 3 ml with 13 mm opening lyo vials and their corresponding butyl rubber stoppers (both from Wheaton) were used for both lyophilization and liquid formulation development. The stoppered vials were capped with Flip-off aluminum caps using a capping device (LW312 Westcapper, The West Company).

Example 2

Lyophilization: Initial Cycle and Formulation Development

There are three main process variables that can be programmed to achieve optimal freeze-drying. Those are shelf temperature, chamber pressure, and lyophilization step duration time. To avoid cake collapse, shelf temperature need to be set at temperatures 2-3° C. below the glass transition or eutectic temperature of the frozen formulation. Both the glass transition and eutectic temperatures of a formulation can be determined by differential scanning calorimetry (DSC) analysis. Chamber pressure is generally set at below the ice vapor pressure of the frozen formulation. The ice vapor pressure is dependent on the shelf temperature and chamber pressure. Too high a chamber pressure will reduce the drying rate by reducing the pressure differential between the ice and the surrounding, while too low a pressure will also slow down drying rate by reducing the heat transfer rate from the shelf to the vials. The development of a lyophilization cycle is closely related with the formulation and the vials chosen for lyophilization. The goal at this stage was to develop a somewhat conservative cycle to be able to successfully freeze dry a number of different formulations. The developed cycles and formulations will be further optimized when viruses are formulated in the formulations. Formulation excipient selection was based on the classical excipients found in most lyophilized pharmaceuticals. The excipients in a lyophilization formulation should provide the functions of bulking, cryoprotection, and lyoprotection. The excipients chosen were mannitol (bulking agent), sucrose (cryo- and lyoprotectant), and human serum albumin (HSA, lyoprotectant). These excipients were formulated in 10 mM Tris+1 mM $MgCl_2$, pH=7.50 at various percentages and filled into the 3 ml vials at a fill volume of 1 ml. To start with, a preliminary cycle was programmed to screen a variety of formulations based on the criteria of residual moisture and physical appearance after drying. The cycle used is plotted in FIG. 1. Extensive screening was carried out by variation of the percentages of the individual excipients. Table 4 shows briefly some of the results.

TABLE 4

Evaluation of Different Formulations Under the Same Cycle

| Formulation M %/S %/HSA % | Appearance | Moisture (% weight) |
|---|---|---|
| 10/5/0.5 | good cake | 0.89 |
| 5/5/0.5 | good cake | 1.5 |
| 3/5/0.5 | loose cake (partial collapse) | 3.4 |
| 1/5/0.5 | no cake (collapse) | 6.4 |

The results suggest that a minimum amount of 3% mannitol is required in the formulation in order to achieve pharmaceutically elegant cake. The percentages of sucrose in the formulation were also examined. No significant effect on freeze-drying was observed at sucrose concentrations of ≦10%. HSA concentration was kept constant to 0.5% during the initial screening stage.

After the evaluation of the formulations, freeze-drying cycle was optimized by changing the shelf temperature, chamber vacuum and the duration of each cycle step. Based on the extensive cycle optimization, the following cycle (cycle #14) was used for further virus lyophilization development.

1. Load sample at room temperature onto shelf.
2. Set shelf temperature to −45° C. and freeze sample. Step time 2 h.
3. Set shelf temperature at −45° C., turn vacuum pump and set vacuum at 400 mT. Step time 5 h.
4. Set shelf temperature at −35° C., set vacuum at 200 mT. Step time 13 h.
5. Set shelf temperature at −22° C., set vacuum at 100 mT. Step time 15 h.
6. Set shelf temperature at −10° C., set vacuum at 100 mT. Step time 5 h.
7. Set shelf temperature at 10° C., set vacuum at 100 mT. Step time 4 h.
8. Vial stoppering under vacuum.

Example 3

Cycle and Formulation Development With Virus in Formulation

Effect of Sucrose Concentration in Formulation. Cycle and formulation were further optimized according to virus recovery after lyophilization analyzed by both HPLC and plaque forming unit (PFU) assays. Table 5 shows the virus recoveries immediate after drying in different formulations using the above drying cycle. Variation of the percentage of sucrose in the formulation had significant effect on virus recoveries.

TABLE 5

Recoveries of Virus After Lyophilization

| Formulation M %/S %/HSA % | Appearance | Residual moisture | Recovery (%) |
|---|---|---|---|
| 6/0/0.5 | good cake | 0.44% | 0 |
| 6/3.5/0.5 | good cake | 2.2% | 56 |
| 6/5/0.5 | good cake | 2.5% | 81 |
| 6/6/0.5 | good cake | 2.7% | 120 |
| 6/7/0.5 | good cake | 2.8% | 120 |
| 6/8/0.5 | good cake | 3.3% | 93 |
| 6/9/0.5 | good cake | 3.7% | 120 |

Residual moisture in the freeze-dried product increased as the sucrose percentage increased. A minimum sucrose concentration of 5% is required in the formulation to maintain a good virus recovery after lyophilization. Similar sucrose effects in formulation that had 5% instead of 6% mannitol were observed. However, good virus recovery immediately after drying does not necessary support a good long-term storage stability. As a result, formulations having 4 different sucrose concentrations of 6, 7, 8, and 9%, were incorporated for further evaluation.

Effect of HSA in Formulation. The contribution of HSA concentrations in the formulation on virus recovery after drying was examined using the same freeze drying cycle. Table 6 shows the results.

TABLE 6

Effects of HSA Concentration on Lyophilization

| Formulation M %/S %/HSA % | Appearance | Residual moisture | Recovery (%) |
|---|---|---|---|
| 6/7/0 | Good cake | 0.98 | 83 |
| 6/7/0.5 | Good cake | 1.24 | 120 |
| 6/7/2 | Good cake | 1.5 | 110 |
| 6/7/5 | Good cake | 1.7 | 102 |

The results indicate that inclusion of HSA in the formulation had positive effect on virus recovery after drying. Concentrations higher than 0.5% did not further improve the virus recovery post drying. As a result, 0.5% HSA is formulated in all the lyophilization formulations.

Cycle Optimization. As indicated in Table 5, relatively high residual moistures were present in the dried product. Although there has not been a known optimal residual moisture for freeze dried viruses, it could be beneficial for long term storage stability to further reduce the residual moisture in the dried product. After reviewing of the drying cycle, it was decided to increase the secondary drying temperature from 10° C. to 30° C. without increasing the total cycle time.

As indicated in Table 7, significant reduction in residual moisture had been achieved in all the formulations without negative effects on virus recoveries. With the improved drying cycle, residual moisture was less than 2% in all the formulations immediately after drying. It is expected that the reduced residual moisture will improve the long-term storage stability of the dried product.

TABLE 7

Effects of Secondary Drying Temperature on Lyophilization

| Formulation M %/S %/HSA % | Secondary drying at 10° C. | | Secondary drying at 30° C. | |
|---|---|---|---|---|
| | Residual moisture (w %) | Recovery (%) | Residual moisture | Recovery |
| 6/6/0.5 | 2.2 | 100 | 0.8 | 93 |
| 6/7/0.5 | 2.5 | 86 | 1.1 | 100 |
| 6/8/0.5 | 2.7 | 83 | 1.3 | 87 |
| 6/9/0.5 | 3.3 | 93 | 1.5 | 86 |
| 5/6/0.5 | 2.3 | 110 | 1.0 | 94 |
| 5/7/0.5 | 2.7 | 88 | 1.2 | 85 |
| 5/8/0.5 | 3.5 | 97 | 1.6 | 88 |
| 5/9/0.5 | 4 | 90 | 1.9 | 86 |

$N_2$ Backfilling (Blanketing). Lyophilization was done similarly as above except that dry $N_2$ was used for gas bleeding for pressure control during the drying and backfilling at the end of the cycle. At the end of a drying run, the chamber was filled with dry $N_2$ to about 80% atmospheric pressure. Subsequently, the vials were stoppered. No difference was noticed between the air and $N_2$ blanketing runs immediate after drying. However, if oxygen present in the vial during air backfilling causes damaging effect (oxidation) on the virus or excipients used during long-term storage, backfilling with dry $N_2$ is likely to ameliorate the damaging effects and improve long term storage stability of the virus.

Removal of Glycerol From Formulation. During the preparation of virus containing formulations, stock virus solution was added to the pre-formulated formulations at a dilution factor of 10. Because of the presence of 10% glycerol in the stock virus solution, 1% glycerol was introduced into the formulations. To examine any possible effect of the presence of 1% glycerol on lyophilization, a freeze drying run was conducted using virus diafiltered into the formulation of 5% (M)/7% (S)/0.5% (HSA). Diafiltration was done with 5 vol. of buffer exchange using a constant volume buffer exchange mode to ensure adequate removal of residual glycerol (99% removal). After diafiltration, virus solution was filled into vials and then lyophilized similarly. Table 8 shows the lyophilization results.

TABLE 8

Lyophilization without Glycerol

| Formulation M %/S %/HSA % | Residual moisture | Recovery (%) |
|---|---|---|
| 5/7/0.5 | 1.0 | 80 |

No significant difference after freeze drying was observed between formulations with and without 1% glycerol. Possible implications of this change on long term storage will be evaluated.

Example 4

Long Term Storage Stability Study

Adp53 virus lyophilized under different formulations and different cycles was placed at −20° C., 4° C., and room temperature (RT) under dark for long term storage stability evaluation. Parameters measured during the stability study were PFU, HPLC viral particles, residual moisture, and vacuum inside vial. The plan is to be able to evaluate virus stability at various conditions for up to one-year storage. Table 6 shows the data after 12-month storage with secondary drying at 10° C. without $N_2$ blanketing. Lyophilized virus is stable at both −20° C. and 4° C. storage for up to 12 months. However, virus was not stable at room temperature storage. More than 50% loss in infectivity was observed at RT after 1-month storage. The reason for the quick loss of infectivity at RT is not clear. However, it is likely that RT is above the glass transition temperature of the dried formulation and resulting in the accelerated virus degradation. A differential scanning caloremitry (DSC) analysis of the formulation could provide very useful information. Pressure change inside the vials during storage was not detected, which indicates that the vials maintained their integrity. The slight increase in residual moisture during storage can be attributed to the release of moisture from the rubber stopper into the dried product.

TABLE 9

Secondary Drying at 10° C.

Formulation Set 10 (6-9)

| Date* | PFU × 10⁹/ml | | | | HPLC Viral Particle (×10¹⁰/ml) | | | | Water Content (W %) | | | |
|---|---|---|---|---|---|---|---|---|---|---|---|---|
| | Set 10-6 | Set 10-7 | Set 10-8 | Set 10-9 | Set 10-6 | Set 10-7 | Set 10-8 | Set 10-9 | Set 10-6 | Set 10-7 | Set 10-8 | Set 10-9 |
| Apr. 11, 1997 | 5.5 | 6.0 | 5.8 | 6.5 | 24.5 | 24.6 | 24.9 | 26.7 | 2.2 | 2.5 | 2.7 | 3.3 |
| May 15, 1997$^a$ | 7.6 | 7.1 | 7.5 | 8.1 | 22.4 | 25.6 | 26.8 | 28.5 | 2.2 | 2.5 | 2.8 | 3.3 |
| May 15, 1997$^b$ | 6.6 | 6.3 | 6.5 | 10.0 | 22.0 | 23.0 | 24.0 | 27.5 | 2.4 | 2.6 | 3.0 | 3.4 |
| May 15, 1996$^c$ | 7.1 | 7.1 | 6.7 | 3.3 | 14.5 | 16.5 | 6.2 | 4.2 | 2.7 | 2.9 | 3.2 | 3.5 |
| Jul. 18, 1997$^a$ | 6.8 | 6.4 | 6.8 | 7.2 | 28.7 | 28.9 | 28.6 | 31.2 | 2.3 | 2.5 | 2.8 | 3.3 |
| Jul. 18, 1997$^b$ | 6.0 | 5.8 | 7.3 | 9.0 | 25.0 | 26.6 | 27.6 | 31.1 | 2.5 | 2.8 | 3.0 | 3.6 |
| Jul. 18, 1997$^c$ | 1.2 | 0.8 | 4.0 | 1.4 | 0.9 | 1.8 | 0.7 | 0.7 | 2.7 | 2.9 | 3.0 | 3.4 |
| Oct. 22, 1997$^a$ | 7.9 | 7.5 | 7.9 | 7.8 | 25.5 | 25.0 | 25.4 | 26.2 | 2.4 | 2.6 | 2.8 | 3.1 |
| Oct. 22, 1997$^b$ | 6.8 | 6.8 | 5.8 | 8.0 | 22.0 | 23.0 | 24.7 | 24.2 | 2.7 | 2.9 | 3.2 | 3.6 |
| Oct. 22, 1997$^c$ | <0.01 | <0.01 | <0.01 | <0.01 | N.D. | N.D. | N.D. | N.D. | 2.7 | 2.9 | 3.1 | 3.4 |
| Apr. 16, 1998$^a$ | 6.0 | 5.8 | 7.1 | 7.2 | 19.3 | 20.3 | 23.5 | 26.1 | 2.4 | 2.6 | 3.0 | 3.4 |

TABLE 9-continued

Secondary Drying at 10° C.

| | | | | | | | | | | | |
|---|---|---|---|---|---|---|---|---|---|---|---|
| Apr. 16, 1998[b] | 5.4 | 7.2 | 6.1 | 6.3 | 21.7 | 22.8 | 22.9 | 24.6 | 2.9 | 3.1 | 3.3 | 3.8 |
| Apr. 16, 1998[c] | 0.0003 | 0.001 | 0.0007 | 0.001 | N.D. | N.D. | N.D. | N.D. | 2.7 | 2.9 | 3.1 | 3.4 |

*Temp  [a](−20° C.)  [b](4° C.)  [c](r.t.)

Controls

| | PFU × 10⁹/ml | | | | HPLC Viral Particle (×10¹⁰/ml) | | | |
|---|---|---|---|---|---|---|---|---|
| Date | Set 10-6 | Set 10-7 | Set 10-8 | Set 10-9 | Set 10-6 | Set 10-7 | Set 10-8 | Set 10-9 |
| Apr. 11, 1997 | 5.5 | 7.0 | 7.0 | 7.0 | 35.5 | 35.8 | 36.0 | 36.9 |

N.D.: not detectable

Formulation set 10: 6%-mannitol, 0.5% HSA, 1% glycerol and different percentages of sucrose in 10 mM-tris buffer pH = 7.5, 1 mM $MgCl_2$

Formulation Set 11 (6-9)

| | PFU × 10⁹/ml | | | | HPLC Viral Particle (×10¹⁰/ml) | | | | Water Content (W %) | | | |
|---|---|---|---|---|---|---|---|---|---|---|---|---|
| Date* | Set 11-6 | Set 11-7 | Set 11-8 | Set 11-9 | Set 11-6 | Set 11-7 | Set 11-8 | Set 11-9 | Set 11-6 | Set 11-7 | Set 11-8 | Set 11-9 |
| May 2, 1997 | 7.0 | 6.0 | 6.3 | 5.8 | 28.5 | 28.8 | 28.4 | 29.5 | 2.3 | 2.7 | 3.5 | 4.0 |
| Jun. 20, 1997[a] | 6.2 | 6.6 | 6.9 | 65 | 26.4 | 25.0 | 27.0 | 27.3 | 2.2 | 2.8 | 34 | 4.6 |
| Jun. 20, 1997[b] | 6.1 | 6.0 | 6.5 | 6.5 | 24.1 | 22.1 | 25.6 | 26.6 | 2.5 | 2.8 | 3.5 | 4.8 |
| Jun. 20, 1997[c] | 3.3 | 3.0 | 1.0 | <0.1 | 20.5 | 17.4 | 5.2 | 9.1 | 2.7 | 3.1 | 3.5 | 4.7 |
| Aug. 18, 1997[a] | 8.0 | 7.2 | 7.5 | 7.6 | 21.6 | 21.8 | 25.3 | 24.9 | 2.3 | 2.8 | 3.7 | 4.9 |
| Aug. 18, 1997[b] | 8.0 | 7.3 | 8.0 | 8.0 | 22.7 | 22.7 | 24.9 | 25.0 | 2.6 | 3 | 3.9 | 4.2 |
| Aug. 18, 1997[c] | <0.1 | <0.1 | <0.1 | <0.1 | N.D. | N.D. | 0.2 | 13.1 | 2.7 | 3.0 | 3.5 | 4.4 |
| Oct. 22, 1997[a] | 79 | 7.5 | 7.9 | 6.7 | 21.0 | 22.0 | 25.1 | 24.0 | 2.4 | 3.0 | 3.9 | 4.4 |
| Oct. 22, 1997[b] | 6.0 | 6.9 | 6.8 | 7.3 | 21.4 | 22.0 | 23.1 | 23.1 | 2.6 | 3.0 | 3.3 | 4.6 |
| Oct. 22, 1997[c] | <0.01 | <0.01 | <0.01 | <0.015 | N.D. | N.D. | N.D. | 9.0 | 2.7 | 2.9 | 3.9 | 5.0 |
| May 8, 1998[a] | 8.3 | 7.5 | 8.0 | 8.7 | 19.0 | 18.2 | 19.9 | 21.1 | 2.6 | 3.1 | 4.0 | 4.6 |
| May 8, 1998[b] | 7.0 | 7.1 | 7.8 | 6.5 | 17.3 | 17.1 | 18.2 | 17.8 | 2.8 | 3.2 | 4.1 | 5.1 |
| May 8, 1998[c] | 0.00033 | 0.000065 | 0.00045 | 0.000016 | N.D. | N.D. | N.D. | N.D. | 2.7 | 2.9 | 4.0 | 4.9 |

*Temp  [a](−20° C.)  [b](4° C.)  [c](R.T.)

Controls

| | PFU × 10⁹/ml | | | | HPLC Viral Particle (×10¹⁰/ml) | | | |
|---|---|---|---|---|---|---|---|---|
| Date | Set 11-6 | Set 11-7 | Set 11-8 | Set 11-9 | Set 11-6 | Set 11-7 | Set 11-8 | Set 11-9 |
| May 2, 1997 | 6.4 | 6.8 | 6.5 | 6.5 | 37.7 | 35.7 | 37.3 | 36.0 |

N.D.: not detectable

Formulation set 11: 5%-mannitol, 0.5% HSA, 1%-glycerol and different percentages of sucrose in 10 mM-tris buffer (pH = 7.5, 1 mM $MgCl_2$)

F11-(6-9)R1-S

TABLE 10

Secondary Drying at 30° C. Without $N_2$ Blanketing

Formulation Set 10 (6-9)

| | PFU × 10⁹/ml | | | | HPLC Viral Particle (×10¹⁰/ml) | | | | Water Content (W %) | | | |
|---|---|---|---|---|---|---|---|---|---|---|---|---|
| Date* | Set 10-6 | Set 10-7 | Set 10-8 | Set 10-9 | Set 10-6 | Set 10-7 | Set 10-8 | Set 10-9 | Set 10-6 | Set 10-7 | Set 10-8 | Set 10-9 |
| May 15, 1997 | 6.5 | 5.6 | 6.1 | 6.0 | 18.0 | 18.6 | 21.9 | 23.3 | 0.8 | 1.1 | 1.3 | 1.5 |
| Jun. 20, 1997[b] | 5.4 | 5.6 | 5.5 | 5.5 | 14.6 | 14.9 | 17.2 | 16.6 | 0.8 | 1.2 | 1.5 | 1.6 |
| Jun. 20, 1997[c] | 4.5 | 5.0 | 5.5 | 6.0 | 10.8 | 11.8 | 15.0 | 15.4 | 1.3 | 1.4 | 1.6 | 1.9 |
| Aug. 18, 1997[b] | 7.0 | 6.7 | 6.8 | 7.0 | 15.3 | 17.1 | 17.9 | 17.7 | 1.3 | 1.5 | 1.5 | 1.7 |
| Aug. 18, 1997[c] | 2.4 | 2.2 | 4.8 | 5.8 | 4.3 | 7.2 | 11.7 | 14.2 | 1.3 | 1.6 | 1.7 | 2.1 |
| Nov. 20, 1997[b] | 5.5 | 5.5 | 5.3 | 5.7 | 21.9 | 21.9 | 27.2 | 26.4 | 1.1 | 1.4 | 1.6 | 1.9 |
| Nov. 20, 1997[c] | 0.5 | 0.9 | 2.3 | 3.1 | 1.5 | 6.3 | 8.8 | 13.5 | 1.3 | 1.7 | 1.8 | 2.2 |
| May 14, 1998[ab] | 4.9 | 4.7 | 5.4 | 6.5 | 9.7 | 11.9 | 12.6 | 14.2 | 1.2 | 1.6 | 2.2 | 1.4 |
| May 14, 1998[c] | 0.000006 | 0.00006 | 0.00004 | 0.000024 | N.D. | N.D. | N.D. | N.D. | 1.4 | 1.6 | 1.3 | 2.0 |

TABLE 10-continued

Secondary Drying at 30° C. Without N₂ Blanketing

Controls

| | PFU × 10⁹/ml | | | | HPLC Viral Particle (×10¹⁰/ml) | | | |
|---|---|---|---|---|---|---|---|---|
| Date | Set 10-6 | Set 10-7 | Set 10-8 | Set 10-9 | Set 10-6 | Set 10-7 | Set 10-8 | Set 10-9 |
| May 15, 1997 | 7.0 | 5.6 | 7.0 | 7.0 | 31.2 | 30.6 | 31.6 | 31.4 |

Formulation Set 11 (6-9)

| | PFU × 10⁹/ml | | | | HPLC Viral Particle (×10¹⁰/ml) | | | | Water Content (W %) | | | |
|---|---|---|---|---|---|---|---|---|---|---|---|---|
| Date* | Set 11-6 | Set 11-7 | Set 11-8 | Set 11-9 | Set 11-6 | Set 11-7 | Set 11-8 | Set 11-9 | Set 11-6 | Set 11-7 | Set 11-8 | Set 11-9 |
| May 22, 1997 | 7.5 | 6.3 | 7.3 | 6.5 | 17.4 | 16.6 | 20.3 | 24.7 | 1.0 | 1.2 | 1.6 | 1.9 |
| Jun. 20, 1997[b] | 5.5 | 6.3 | 6.0 | 7.5 | 14.8 | 16.1 | 17.5 | 21.1 | 1.2 | 1.3 | 1.7 | 1.8 |
| Jun. 20, 1997[c] | 5.0 | 6.0 | 6.0 | 7.5 | 12.6 | 14.9 | 17.2 | 20.3 | 1.4 | 1.6 | 1.9 | 2.0 |
| Aug. 18, 1997[b] | 6.3 | 6.7 | 68 | 7.5 | 15.7 | 17.2 | 18.5 | 22.6 | 1.2 | 1.5 | 1.8 | 1.9 |
| Aug. 18, 1997[c] | 3.3 | 4.5 | 5.5 | 7.0 | 7.4 | 10.5 | 15.8 | 21.2 | 1.6 | 1.7 | 1.9 | 2.2 |
| Nov. 20, 1997[b] | 5.3 | 5.6 | 5.3 | 6.6 | 22.6 | 26.4 | 30.0 | 35.0 | 1.2 | 1.4 | 1.9 | 1.9 |
| Nov. 20, 1997[c] | 0.8 | 1.9 | 3.0 | 0.1 | 3.2 | 9.6 | 18.3 | 1.3 | 1.6 | 1.7 | 2.0 | 2.1 |
| May 14, 1998[b] | 6.7 | 7.2 | 6.9 | 7.6 | 12.4 | 13.9 | 15.5 | 18.5 | 1.3 | 1.6 | 2.0 | 2.2 |
| May 14, 1998[c] | 0.0013 | 0.00005 | 0.00031 | 0.00045 | N.D. | N.D. | N.D. | N.D. | 1.6 | 1.8 | 1.6 | 2.0 |

Controls

| | PFU × 10⁹/ml | | | | HPLC Viral Particle (×10¹⁰/ml) | | | |
|---|---|---|---|---|---|---|---|---|
| Date | Set 11-6 | Set 11-7 | Set 11-8 | Set 11-9 | Set 11-6 | Set 11-7 | Set 11-8 | Set 11-9 |
| May 22, 1997 | 8.0 | 7.4 | 8.3 | 7.6 | 26.7 | 27.6 | 27.5 | 32.4 |

*Temp  
[ab](4° C.)  
[a](−20° C.)  
[b](4° C.)  
[c](R.T.)  
Formulation set 10: 6%-mannitol, 0.5% HSA, 1%-glycerol and different percentages of sucrose in 10 mM-tris buffer (pH = 7.5, 1 mM MgCl₂)  
F10(6-9)R2-S  
Formulation set 11: 5%-mannitol, 0.5% HSA, 1%-glycerol and different percentages of sucrose in 10 mM-tris buffer (pH = 7.5, 1 mM MgCl₂)  
F11-(6-9)R2-S

TABLE 11

Secondary Drying at 30° C. With N₂ Blanketing

Formulation Set 10 (6-9) + Adp53

| | PFU × 10⁹/ml | | | | HPLC Viral Particle (×10¹⁰/ml) | | | | Water Content (W %) | | | |
|---|---|---|---|---|---|---|---|---|---|---|---|---|
| Date* | Set 10-6 | Set 10-7 | Set 10-8 | Set 10-9 | Set 10-6 | Set 10-7 | Set 10-8 | Set 10-9 | Set 10-6 | Set 10-7 | Set 10-8 | Set 10-9 |
| Jun. 13, 1997 | 3.4 | 4.3 | 4.1 | 4.2 | 16.0 | 16.5 | 16.1 | 18.1 | 0.8 | 1.1 | 1.3 | 1.4 |
| Jul. 18, 1997[b] | 6.3 | 6.3 | 6.0 | 6.0 | 17.9 | 19.5 | 19.9 | 20.6 | 0.9 | 1.2 | 1.4 | 1.6 |
| Jul. 18, 1997[c] | 4.1 | 5.5 | 5.0 | 5.5 | 11.4 | 15.5 | 18.2 | 20.6 | 1.2 | 1.4 | 1.7 | 1.8 |
| Sep. 16, 1997[b] | 4.2 | 5.5 | 4.5 | 5.1 | 15.3 | 16.1 | 16.4 | 17.8 | 1.0 | 1.3 | 1.5 | 1.7 |
| Sep. 16, 1997[c] | 0.7 | 1.2 | 5.0 | 4.0 | 2.9 | 5.0 | 9.5 | 13.0 | 1.3 | 1.5 | 1.8 | 2.0 |
| Dec. 4, 1997[b] | 5.5 | 5.3 | 5.4 | 5.9 | 16.1 | 16.2 | 18.1 | 18.5 | 1.1 | 1.4 | 1.6 | 1.7 |
| Dec. 4, 1997[c] | 0.3 | 0.5 | 2.5 | 3.4 | N.D. | 1.7 | 4.7 | 8.8 | 1.4 | 1.6 | 1.8 | 2.0 |
| Jun. 29, 1998[ab] | 3.8 | 5.1 | 5.3 | 5.4 | 10.6 | 10.8 | 12.0 | 12.9 | 1.3 | 1.5 | 1.8 | 1.9 |
| Jun. 29, 1998[c] | 0.00003 | 0.00006 | 0.0001 | 0.0001 | N.D. | N.D. | N.D. | N.D. | 1.4 | 1.6 | 1.7 | 1.8 |

Controls

| | PFU × 10⁹/ml | | | | HPLC Viral Particle (×10¹⁰/ml) | | | |
|---|---|---|---|---|---|---|---|---|
| Date | Set 10-6 | Set 10-7 | Set 10-8 | Set 10-9 | Set 10-6 | Set 10-7 | Set 10-8 | Set 10-9 |
| Jun. 13, 1997 | 4.7 | 3.8 | 5.5 | 6.2 | 26.0 | 26.2 | 27.4 | 27.5 |

TABLE 11-continued

Secondary Drying at 30° C. With $N_2$ Blanketing

Formulation set 11 (6-9) + Adp53

| Date* | PFU × 10⁹/ml | | | | HPLC Viral Particle (×10¹⁰/ml) | | | | Water Content (W %) | | | |
|---|---|---|---|---|---|---|---|---|---|---|---|---|
| | Set 11-6 | Set 11-7 | Set 11-8 | Set 11-9 | Set 11-6 | Set 11-7 | Set 11-8 | Set 11-9 | Set 11-6 | Set 11-7 | Set 11-8 | Set 11-9 |
| Jun. 13, 1997 | 3.4 | 4.2 | 3.6 | 4.4 | 16.1 | 16.3 | 18.4 | 19.3 | 0.9 | 1.3 | 1.8 | 1.9 |
| Jul. 18, 1997[b] | 5.5 | 6.2 | 6.5 | 6.2 | 18.0 | 19.5 | 23.0 | 23.9 | 1.0 | 1.4 | 1.8 | 2.1 |
| Jul. 18, 1997[c] | 3.7 | 6.0 | 6.7 | 7.3 | 13.7 | 18.7 | 21.8 | 22.8 | 1.3 | 1.7 | 2.0 | 2.2 |
| Sep. 16, 1997[b] | 3.9 | 4 | 4.6 | 6 | 15.6 | 17.3 | 19.5 | 20.6 | 1.3 | 1.5 | 1.9 | 2.1 |
| Sep. 16, 1997[c] | 0.78 | 2.2 | 4.0 | 5.3 | 3.6 | 6.8 | 13.8 | 14.6 | 1.5 | 1.9 | 2.3 | 2.4 |
| Dec. 4, 1997[b] | 4.6 | 5.3 | 8.0 | 6.1 | 15.7 | 18.2 | 21.4 | 21.6 | 1.2 | 1.6 | 2.1 | 2.2 |
| Dec. 4, 1997[c] | 0.4 | 0.6 | 0.3 | 0.01 | N.D. | N.D. | 1.7 | N.D. | 1.6 | 1.8 | 2.1 | 2.1 |
| Jun. 29, 1998[ab] | 4.9 | 5.0 | 5.4 | 6.4 | 11.4 | 14.2 | 13.7 | 16.0 | 1.5 | 1.7 | 2.1 | 2.6 |
| Jun. 29, 1998[c] | 0.0001 | 0.00015 | 0.00085 | 0.0012 | N.D. | ND. | N.D. | N.D. | 1.6 | 1.7 | 2.2 | 2.3 |

| | Controls | | | | | | | |
|---|---|---|---|---|---|---|---|---|
| | PFU × 10⁹/ml | | | | HPLC Viral Particle (×10¹⁰/ml) | | | |
| Date | Set 11-6 | Set 11-7 | Set 11-8 | Set 11-9 | Set 11-6 | Set 11-7 | Set 11-8 | Set 11-9 |
| Jun. 13, 1997 | 4.5 | 5.0 | 4.0 | 5.0 | 26.5 | 26.9 | 26.6 | 27.1 |

*Temp.
[ab](4° C.)
[c](R.T.)
Formulation set 10: 6%-mannitol, 0.5% HSA, 1%-glycerol and different percentages of sucrose in 10 mM-tris buffer (pH: 7.5, 1 mM $MgCl_2$)
Formulation set 11: 6%-mannitol, 0.5% HSA, 1%-glycerol and different percentages of sucrose in 10 mM-tris buffer (pH = 7.5, 1 mM $MgCl_2$)
F11-(6-9)R3-S

TABLE 12

Aqueous Formulation Set #1

| Date (Storage Conds.) | 10%-G | 5%-S + 5%-HSA | 5%-S + 1%-PEG | 5%-T + 1%-PEG |
|---|---|---|---|---|
| | PFU × 10⁹/ml | | | |
| Aug. 1, 1997 | 5.8 | 4.7 | 4.3 | 4.4 |
| Aug. 28, 1997 (4° C., $N_2$) | 5.8 | 5.8 | 6.4 | 6.3 |
| Aug. 28, 1997 (4° C.,. Air) | 5.0 | 5.9 | 6.0 | 5.9 |
| Aug. 28, 1997 (R.T., $N_2$) | 4.4 | 4.8 | 5.0 | 6.0 |
| Aug. 28, 1997 (R.T., Air) | 4.3 | 5.0 | 5.0 | 5.6 |
| Oct. 30, 1997 (4° C., $N_2$) | 3.8 | 4.0 | 4.7 | 3.8 |
| Oct. 30, 1997 (4° C. Air) | 3.0 | 4.1 | 3.7 | 4.7 |
| Oct. 30, 1997 (R.T., N2) | 1.5 | 3.4 | 3.5 | 3.6 |
| Oct. 30, 1997 (R.T., Air) | 1.5 | 3.6 | 2.2 | 3.1 |
| Jan. 12, 1998 (4° C., $N_2$) | 3.2 | 4.1 | 3.3 | 3.4 |
| Jan. 12, 1998 (4° C., Air) | 1.5 | 3.8 | 3.9 | 3.4 |
| Jan. 12, 1998 (R.T., $N_2$) | 0.1 | 1.4 | 0.7 | 0.7 |
| Jan. 12, 1998 (R.T., Air) | 0.4 | 1.6 | 1.0 | 0.4 |
| Apr. 30, 1998 (4° C., $N_2$) | 0.08 | 4.3 | 4.0 | 5.3 |
| Apr. 30, 1998 (4° C., Air) | 1.5 | 3.6 | 4.4 | 4.5 |
| Apr. 30, 1998 (R.T., $N_2$) | 0.0025 | 0.23 | 0.11 | 0.17 |
| Apr. 30, 1998 (R.T., Air) | 0.0015 | 0.21 | 0.063 | 0.007 |
| Feb. 5, 1999 (4° C., $N_2$) | 0.0005 | 5.8 | 4.1 | 3.9 |
| Feb. 5, 1999 (4° C., Air) | 0.02 | 4.7 | 4.3 | 4.5 |
| Feb. 5, 1999 (R.T., $N_2$) | <$10^2$ | 0.0007 | <$10^4$ | 0.0002 |
| Feb. 5, 1999 (R.T., Air) | 2 × $10^2$ | 0.0002 | 0.0003 | 2 × $10^3$ |
| | HPLC Viral Particle (×10¹⁰/ml) | | | |
| Aug. 1, 1997 | 16.9 | 14.5 | 16.1 | 16.7 |
| Aug. 28, 1997 (4° C., $N_2$) | 13.3 | 14.9 | 13.8 | 13.4 |
| Aug. 28, 1997 (4° C., Air) | 12.9 | 14.2 | 12.9 | 12.9 |
| Aug. 28, 1997 (R.T., $N_2$) | 12.6 | 14.5 | 13.5 | 12.9 |
| Aug. 28, 1997 (R.T., Air) | 12.3 | 13.7 | 13.0 | 13.0 |
| Oct. 30, 1997 (4° C., $N_2$) | 14.0 | 15.5 | 14.7 | 14.8 |
| Oct. 30, 1997 (4° C., Air) | 12.6 | 14.9 | 14.3 | 14.4 |
| Oct. 30, 1997 (R.T., $N_2$) | 13.8 | 15.1 | 14.6 | 14.4 |
| Oct. 30, 1997 (R.T., Air) | 12.7 | 14.7 | 14.8 | 14.4 |
| Jan. 12, 1998 (4° C., $N_2$) | 7.3 | 11.1 | 9.5 | 9.5 |
| Jan. 12, 1998 (4° C., Air) | 7.7 | 10.8 | 10.2 | 10.0 |
| Jan. 12, 1998 (R.T., N2) | 10.0 | 10.8 | 11.1 | 10.4 |

TABLE 12-continued

Aqueous Formulation Set #1

| Date (Storage Conds.) | 10%-G | 5%-S + 5%-HSA | 5%-S + 1%-PEG | 5%-T + 1%-PEG |
|---|---|---|---|---|
| Jan. 12, 1998 (R.T., Air) | 9.9 | 11.0 | 10.0 | 10.4 |
| Apr. 30, 1998 (4° C., $N_2$) | 5.1 | 12.3 | 12.3 | 12.1 |
| Apr. 30, 1998 (4° C., Air) | 5.0 | 11.6 | 11.8 | 11.9 |
| Apr. 30, 1998 (R.T., $N_2$) | 11.1 | 12.3 | 12.6 | 12.5 |
| Apr. 30, 1998 (R.T., Air) | 11.0 | 12.4 | 12.3 | 11.0 |
| Feb. 5, 1999 (4° C., $N_2$) | 3.4 | 5.8 | 11.4 | 11.0 |
| Feb. 5, 1999 (4° C., Air) | 3.9 | 7.1 | 11.0 | 11.2 |
| Feb. 5, 1999 (R.T., $N_2$) | 10.1 | 7.9 | 8.5 | 10.9 |
| Feb. 5, 1999 (R.T., Air) | 9.7 | 7.1 | 10.3 | 9.3 |

G: glycerol
S: sucrose
PEG: PEG-3500
T: trehalose
Glycerol: 10% glycerol in DPBS buffer
Other formulations are in 10 mM-tris buffer with 0.15 M-NaCl and 1 mM-$MgCl_2$ (pH = 8.2).

TABLE 13

Aqueous Formulation Set #2

| | PFU × $10^9$/ml | | | | | | |
|---|---|---|---|---|---|---|---|
| Date (Temp.) | AQF2-1 | AQF2-2 | AQF2-3 | AQF2-4 | AQF2-5 | AQF2-6 | AQF2-7* |
| Sep. 25, 1997 | 2.8 | 2.8 | 2.8 | 3.0 | 2.8 | 2.8 | 2.7 |
| Nov. 05, 1997 (4° C.) | 2.3 | 3.2 | 2.4 | 3.6 | 2.7 | 2.0 | 3.6 |
| Nov. 05, 1997 (R.T.) | 1.4 | 1.9 | 1.3 | 1.5 | 2.4 | 2.5 | 3.1 |
| Dec. 12, 1997 (4° C.) | 2.2 | 0.1 | 2.4 | 2.7 | 2.1 | 2.1 | 3.2 |
| Jan. 09, 1998 (R.T.) | 1.2 | 0.1 | 0.2 | 1.2 | 0.2 | 0.1 | 1.3 |

| | PFU × $10^9$/ml | | | | |
|---|---|---|---|---|---|
| Date (Temp.) | AQF2-8* | AQF2-9* | AQF2-10* | AQF2-11* | AQF2-12 |
| Sep. 25, 1997 | 2.8 | 2.7 | 3.3 | 3.1 | 2.7 |
| Nov. 05, 1997 (4° C.) | 3.8 | 2.7 | 3.0 | 3.5 | 2.5 |
| Nov. 05, 1997 (R.T.) | 3.3 | 3.1 | 4.1 | 2.8 | 1.1 |
| Dec. 12, 1997 (4° C.) | 2.1 | 3.0 | 3.0 | 3.4 | 2.9 |
| Jan. 09, 1998 (R.T.) | 1.1 | 0.2 | 0.1 | 20 | 1.1 |

| | HPLC viral particle (×$10^{10}$/ml) | | | | | | |
|---|---|---|---|---|---|---|---|
| Date (Temp.) | AQF2-1 | AQF2-2 | AQF2-3 | AQF2-4 | AQF2-5 | AQF2-6 | AQF2-7 |
| Sep. 25, 1997 | 10.9 | 9.6 | 9.7 | 11.3 | 10.7 | 10.6 | 10.9 |
| Nov. 05, 1997 (4° C.) | 7.9 | 7.6 | 8.7 | 8.8 | 8.9 | 7.5 | 8.6 |
| Nov. 05, 1997 (R.T.) | 8.2 | 6.6 | 7.6 | 8.6 | 7.7 | 9.3 | 9.0 |
| Dec. 12, 1997 (4° C.) | 6.7 | 1.5 | 8.0 | 6.9 | 5.2 | 7.5 | 7.5 |
| Dec. 17, 1997 (R.T.) | 7.0 | 1.2 | 7.0 | 7.5 | 4.1 | 7.1 | 7.0 |

| | HPLC viral particle ×$10^{10}$/ml | | | | |
|---|---|---|---|---|---|
| Date (Temp.) | AQF2-8 | AQF2-9 | AQF2-10 | AQF2-11 | AQF2-12 |
| Sep. 25, 1997 | 10.8 | 10.7 | 11.4 | 11.8 | 10.7 |
| Nov. 05, 1997 (4° C.) | 9.1 | 9.2 | 10.3 | 11.2 | 9.6 |
| Nov. 05, 1997 (R.T.) | 8.0 | 9.3 | 10.3 | 11.1 | 9.6 |
| Dec. 12, 1997 (4° C.) | 6.1 | 7.6 | 8.8 | 7.3 | 7.7 |
| Dec. 17, 1997 (R.T.) | 3.0 | 8.2 | 7.6 | 8.4 | 7.5 |

| Aqueous Formulation Set 2 | | | | | | | |
|---|---|---|---|---|---|---|---|
| Excipients | AQF2-1 | AQF2-2 | AQF2-3 | AQF2-4 | AQF2-5 | AQF2-6 | AQF2-7 |
| mannitol (W %) | 5 | 5 | 5 | | | | 5 |
| sucrose (W %) | | | | 5 | 5 | 5 | 5 |
| glycine (M) | 0.25 | | | 0.25 | | | 0.25 |
| arginine (M) | | 0.25 | | | 0.25 | | |
| urea (W %) | | | 1 | | | 1 | |
| peg (w %) | | | | | | | |

TABLE 13-continued

| Excipients | AQF2-8 | AQF2-9 | AQF2-10 | AQF2-11 | AQF2-12 |
|---|---|---|---|---|---|
| mannitol (W %) | 5 | 5 | 5 | 5 | |
| sucrose (W %) | 5 | 5 | 5 | 5 | 10 |
| glycine (M) | | | | 0.25 | 0.25 |
| arginine (M) | 0.25 | | | 0.25 | |
| urea (W %) | | 1 | | 1 | |
| peg (w %) | | | 1 | 1 | |

*Gave better recovery.
Formulations are in 10 mM-tris buffer (pH = 7.5) which consists of 1% glycerol and 1 mM $MgCl_2$.
The formulations are stored at 4° C. and room temperature under nitrogen.

TABLE 14

Aqueous Formulation Set #3

| | PFU × $10^9$ | | | | HPLC Viral Particle (×$10^9$/ml) | | | |
|---|---|---|---|---|---|---|---|---|
| Date (temp.) | F10-7 | F10-8 | F11-7 | F11-8 | F10-7 | F10-8 | F11-7 | F11-8 |
| Oct. 3, 1997 | 2.2 | 3.3 | 2.1 | 2.8 | 12.1 | 12.0 | 11.8 | 12.0 |
| Nov. 6, 1997 (−20° C.) | 3.4 | 4.0 | 2.8 | 3.4 | 10.6 | 10.5 | 10.1 | 10.3 |
| Nov. 6, 1997 (4° C.) | 3.5 | 3.6 | 4.3 | 2.8 | 10.0 | 9.7 | 9.9 | 10.3 |
| Jan. 15, 1998 (−20° C.) | 3.8 | 4.8 | 3.2 | 3.7 | 7.3 | 7.4 | 7.7 | 8.0 |
| Jan. 15, 1998 (4° C.) | 3.5 | 3.1 | 2.9 | 3.1 | 7.5 | 7.4 | 7.6 | 7.5 |

| Excipients | F10-7 | F10-8 | F11-7 | F11-8 |
|---|---|---|---|---|
| mannitol (W %) | 6 | 6 | 5 | 5 |
| sucrose (VV %) | 7 | 8 | 7 | 8 |
| HSA (W %) | 0.5 | 0.5 | 0.5 | 0.5 |
| glycerol (W %) | 1 | 1 | 1 | 1 |
| $MgCl_2$ (mM) | 1 | 1 | 1 | 1 |

TABLE 15

Liquid formulation set #4

| | PFU (×$10^9$/ml) | | | | | | |
|---|---|---|---|---|---|---|---|
| Date (Temp.) | AQF4-1 | AQF4-2 | AQF4-3 | AQF4-4 | AQF4-5 | AQF4-6 | AQF4-7 |
| Jan. 13, 1998 | 3.0 | 2.5 | 3.6 | 3.4 | 2.7 | 3.1 | 3.4 |
| Feb. 16, 1998 (4° C.) | 2.5 | 3.2 | 3.3 | 2.9 | 2.6 | 2.9 | 2.6 |
| Feb. 16, 1998 (R.T.) | 1.8 | 2.7 | 1.6 | 3.6 | 2.6 | 1.6 | 1.7 |
| Apr. 10, 1998 (4° C.) | 2.2 | 2.0 | 2.6 | 3.0 | 2.4 | 1.9 | 2.2 |
| Apr. 10, 1998 (R.T.) | 0.4 | 0.4 | 0.3 | 0.5 | 0.4 | <0.1 | 1.1 |
| Jul. 24, 1998 (4° C.) | 2.4 | 2.8 | 2.6 | 3.5 | 1.9 | 2.2 | 2.6 |
| Jul. 24, 1998 (R.T.) | 0.002 | 0.005 | 0.006 | 0.005 | 0.005 | 0.005 | 0.001 |
| Jan. 8, 1999 (4° C.) | 2.9 | 2.4 | 2.1 | 2.6 | 2.0 | 2.2 | 2.1 |
| Jan. 8, 1999 (R.T.) | 0.0002 | 0.0004 | 0.0004 | 0.0002 | 0.0004 | 0.0004 | 0.00006 |

| | HPLC Viral Particles (×$10^{10}$/ml) | | | | | | |
|---|---|---|---|---|---|---|---|
| Date (Temp.) | AQF4-1 | AQF4-2 | AQF4-3 | AQF4-4 | AQF4-5 | AQF4-6 | AQF4-7 |
| Jan. 13, 1998 | 7.2 | 8.8 | 9.2 | 9.0 | 7.8 | 7.9 | 9.1 |
| Feb. 16, 1998 (4° C.) | 7.5 | 9.3 | 9.2 | 9.5 | 8.2 | 8.4 | 9.6 |
| Feb. 16, 1998 (R.T.) | 6.8 | 9.0 | 9.5 | 9.0 | 8.7 | 8.4 | 9.3 |
| Apr. 10, 1998 (4° C.) | 7.1 | 9.2 | 9.6 | 9.6 | 8.9 | 9.1 | 9.9 |
| Apr. 10, 1998 (R.T.) | 7.5 | 9.5 | 10.1 | 9.7 | 8.9 | 8.9 | 9.5 |
| Jul. 24, 1998 (4° C.) | 8.1 | 9.9 | 11.1 | 10.3 | 9.2 | 7.4 | 9.3 |
| Jul. 24, 1998 (R.T.) | 7.3 | 3.0 | 10.7 | 8.9 | 10.4 | 10.45 | 3.5 |
| Jan. 8, 1999 (4° C.) | 7.8 | 10.3 | 10.3 | 10.1 | 8.7 | 1.7 | 9.5 |
| Jan. 8, 1999 (R.T.) | 8.4 | 11.0 | 11.3 | 11.0 | 9.7 | 10.4 | 9.4 |

| Excipients | AQF4-1 | AQF4-2 | AQF4-3 | AQF4-4 | AQF4-5 | AQF4-6 | AQF4-7 |
|---|---|---|---|---|---|---|---|
| Mannitol (w %) | 5 | 5 | 5 | 5 | 5 | 5 | 5 |
| Sucrose (w %) | 5 | 5 | 5 | 5 | 5 | 5 | 5 |
| Tween-80 (w %) | | 0.02 | 0.1 | 0.5 | | | |
| Chap (w %) | | | | | 0.02 | 0.1 | 0.5 |

Buffer: 10 mM Tris + H0.15 M NaCl + 1 mM MgCl2, pH = 8.2
Formulations were blanketed with $N_2$.

observed at −20° C. and 4° C. storage conditions, and to

Table 10 and Table 11 show the storage stability data with secondary drying at 30° C. without and with $N_2$ backfilling, respectively. Because of the nearly identical stability reduce the consumption of virus, −20° C. was not included in the long-term storage stability study. Similar to the samples dried with secondary drying at 10° C., virus is stable at 4° C. but not stable at RT. However, relative better stability was observed at RT storage than those dried at 10° C. secondary drying. This is likely to be the result of the lower residual moisture attained at 30° C. secondary drying. This result suggests that residual moisture is an important parameter that affects storage stability during long term storage.

HPLC viral particle recoveries are consistently lower than virus recoveries calculated from PFU assay immediate after drying. The reason for the discrepancy is not clear. However, it is likely to be related to possible virus aggregation during freeze-drying. Electron microscopy evaluation is being carried out to examine possible virus aggregation after lyophilization. During storage, HPLC analysis indicates that virus is stable at both −20° C. and 4° C. storage and not stable at RT, which is consistent with the results from PFU assay.

Example 5

HSA Alternatives

The presence of HSA in the formulations could be a potential regulatory concern. As a result, a variety of excipients have been evaluated to substitute HSA in the formulation. The substitutes examined included PEG, amino acids (glycine, arginine), polymers (polyvinylpyrrolidone), and surfactants (Tween-20 and Tween-80). These HSA substitutes are, however, suboptimal relative to HSA. Effort on further development was minimal.

Example 6

Liquid Formulation

Concurrent with the development of lyophilization of Adp53 product, experimentation was carried out to examine the possibility of developing a liquid formulation for Adp53 product. The goal was to develop a formulation that can provide enough stability to the virus when stored at above freezing temperatures. Four sets of liquid formulations have been evaluated. In the first set of formulation, the current 10% glycerol formulation was compared to HSA and PEG containing formulations. In the second set of formulation, various amino acids were examined for formulating Adp53. In the third set of formulation, the optimal formulation developed for lyophilization was used to formulate Adp53 in a liquid form. In the fourth set of formulation, detergents were evaluated for formulating Adp53. Viruses formulated with all those different formulations are being tested for long term storage stability at −20° C., 4° C., and RT.

Liquid Formulation Set #1

HSA containing formulation (5% sucrose+5% HSA in 10 mM Tris buffer, 150 mM NaCl, and 1 mM $MgCl_2$, pH=8.20 buffer) was compared with 10% glycerol in DPBS buffer and sucrose/PEG and Trehalose/PEG formulations. PEG has been recommended as a good preferential exclusion agent in formulations (Wong and Parasrampurita, 1997). It is included in this set of formulation to examine whether it can provide stabilization effect on Adp53. Formulations were filled into the 3 ml lyo vials at a fill volume of 0.5 ml. Vials were capped under either atmospheric or $N_2$ blanketing conditions to examine any positive effects $N_2$ blanketing may have on long term storage stability of Adp53. To ensure adequate degassing from the formulation and subsequent $N_2$ blanketing, the filled vials was partially stoppered with lyo stoppers and loaded onto the shelf of the lyophilizer under RT. The lyophilizer chamber was closed and vacuum was established by turning on the vacuum pump. The chamber was evacuated to 25 in Hg. Then the chamber was purged completely with dry $N_2$. The evacuation and gassing were repeated twice to ensure complete $N_2$ blanketing. $N_2$ blanketed vials were placed with the non-$N_2$ blanketed vials at various storage conditions for storage stability evaluation. Table 12 shows the analysis data for up to 18 months storage at 4° C. and RT.

Statistically significant drops in virus PFU and HPLC viral particles were observed for 10% glycerol formulation after 3 months storage at both 4° C. and RT. No statistically significant virus degradation was observed for all other formulations at 4° C. storage. However, decrease in virus infectivity was observed when stored at RT.

Liquid Formulation Set #2

Various combinations of amino acids, sugars, PEG and urea were evaluated for Adp53 stabilization during long storage. Table 13 shows the 12-month stability data. The results indicate that combination of 5% mannitol and 5% sucrose with other excipients gave better storage stability at RT for one month. Adp53 is most stable in formulation has all the excipients. In this set of formulation, no human or animal derived excipients were included. It is our expectation to develop a liquid formulation without including any proteins derived from either human or animal origins.

Liquid Formulation Set #3

The optimal formulations developed for lyophilization was evaluated for formulating Adp53 in a liquid form. This approach would be a good bridging between liquid formulation and lyophilization if satisfactory Adp53 stability can be achieved using lyophilization formulation for liquid fill. Filled samples were stored at −20° C. and 4° C. for stability study. Table 14 shows the 3-month stability data. Virus is stable at both −20° C. and 4° C. for the four different formulations. This is in agreement with the results from formulation set #2, which suggests that better virus stability is expected with the presence of both mannitol and sucrose in the formulation. Longer time storage stability data is being accrued.

Liquid Formulation Set #4

Detergents have been used in the formulations for a variety of recombinant proteins. In this set of formulation, various concentrations of detergents were examined for formulating Adp53. The detergents used were non-ionic (Tween-80) and zwitterionic (Chap). Table 15 shows the 12-month stability data. Virus is stable at 4° C. storage. No significant difference in virus stability at 4° C. was observed among the formulations tested. Similar to formulation set #2, no exogenous protein is included in this set of formulation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,797,368
U.S. Pat. No. 5,139,941
U.S. Pat. No. 5,552,309
U.S. Pat. No. 5,789,244
U.S. Ser. No. 08/975,519
EPO 0273085
WO 94/17178
WO 98/35554
Arap et al., *Cancer Res.*, 55:1351-1354, 1995.
Baichwal et al., "Vectors for gene transfer derived from animal DNA viruses: Transient and stable expression of transferred genes," In: *Gene transfer*, Kucherlapati R, ed., New York: Plenum Press, pp. 117-148, 1986.
Bourlais, Acar, Zia, Sado, Needham, Leverge, "Ophthalmic drug delivery systems-recent advances," *Prog. Retin. Eye Res.*, 17:33-58, 1998.
Caldas et al., *Nat. Genet.*, 8:27-32, 1994.
Caldovic and Hackett Jr., "Development of position-independent expression vectors and their transfer into transgenic fish," *Mol. Mar. Biol. Biotechnol.*, 4(1):51-61, 1995.
Carver, Dalrymple, Wright, Cottom, Reeves, Gibson, Keenan, Barrass, Scott, Colman, et al., "Transgenic livestock as bioreactors: stable expression of human alpha-1-antitrypsin by a flock of sheep," *Biotechnology NY*, 11(11): 1263-1270, 1993.
Casey et al., *Oncogene*, 6:1791-1797, 1991.
Chang et al., "Foreign gene delivery and expression in hepatocytes using a hepatitis B virus vector," *Hepatology*, 14:134 A, 1991.
Chen and Okayama, "High-efficiency transfection of mammalian cells by plasmid DNA," *Mol. Cell Biol.*, 7:2745-2752, 1987.
Cheng et al., *Cancer Res.*, 54:5547-5551, 1994.
Cheung et al., *Biochem. J*, 295:427-435, 1993c.
Cheung et al., *J. Biol. Chem.*, 268:24303-24310, 1993a.
Cheung et al., *J. Biol. Chem.*, 268:6139-6146, 1993b.
Chikada and Jones, "Study of gene delivery in a rabbit vein graft model. Improvement of the efficiency of gene transfer into vein grafts," *Jpn J Thorac Cardiovasc Surg.*, 47(5): 204-9, May 1999.
Chinnadurai et al., "Enhanced infectivity of adenovirus type 2 DNA and a DNA-protein complex," *J Virol.*, 26(1):195-9, April 1978.
Clark, Voulgaropoulou, Fraley, Johnson, "Cell lines for the production of recombinant adeno-associated virus," *Human Gene Therapy*, 6:1329-1341, 1995.
Coffey, M. C., Strong, J. E., Forsyth, P. A. and Lee, P. K., "Reovirus Therapy of Tumors with Activated Ras Patway," *Science*, 282:1332-1334, 1998.
Coffin, "Retroviridae and their replication," In: *Virology*, Fields et al. (eds.), New York: Raven Press, pp. 1437-1500, 1990.
Colberre-Garapin et al., *J. Mol. Biol.*, 150:1, 1981.
Corveleyn and Remon, "Maltodextrins as lyoprotectants in the lyophilization of a model protein, LDH," *Pharm. Res.*, 13(1):146-150, 1996.
Couch et al., "Immunization with types. 4 and 7 adenovirus by selective infection of the intestinal tract," *Am. Rev. Resp. Dis.*, 88:394-403, 1963.
Coupar et al., "A general method for the construction of recombinant vaccinia virus expressing multiple foreign genes," *Gene*, 68:1-10, 1988.
Croyle, Roessler, Davidson, Hilfinger, Amidon, "Factors that influence stability of recombinant adenoviral preparations for human gene therapy," *Pharm. Dev. Technol.*, 3(3):373-383, 1998.
Curiel, "Gene transfer mediated by adenovirus-polylysine DNA complexes," In: *Viruses in Human Gene Therapy*, J.-M. H. Vos (Ed.), Carolina Academic Press, Durham, N. C., pp. 179-212, 1994.
Edelman and Crossin, *Annu. Rev. Biochem.*, 60:155-190, 1991
Edelman, *Annu. Rev. Biochem.*, 54:135-169, 1985.
Ferkol et al., *FASEB J*, 7:1081-1091, 1993.
Flotte, Afione, Conrad, McGrath, Solow, Oka, Zeitlin, Guggino, and Carter, "Stable in vivo expression of the cystic fibrosis transmembrane conductance regulator with an adeno-associated virus vector," *Proc. Natl. Acad. Sci. USA*, 90:10613-10617, 1993.
Flotte, Barraza-Ortiz, Solow, Afione, Carter, and Guggino, "An improved system for packaging recombinant adeno-associated virus vectors capable of in vivo transduction," *Gene Therapy*, 2:29-37, 1995.
Flotte, Solow, Owens, Afione, Zeitlin, and Carter, "Gene expression from adeno associated virus vector in airway epithelial cells," *Am. J. Respir. Cell Mol. Biol.*, 7:349-356, 1992.
Fried and Bromberg, "Factors that affect the stability of protein-DNA complexes during gel electrophoresis," *Electrophoresis*, 18(1):6-11, 1997.
Friedmann, "Progress toward human gene therapy," *Science*, 244:1275-1281, 1989.
Ghosh-Choudhury et al., "Protein IX, a minor component of the human adenovirus capsid, is essential for the packaging of full-length genomes," *EMBO J.*, 6:1733-1739, 1987.
Gomez-Foix et al., "Adenovirus-mediated transfer of the muscle glycogen phosphorylase gene into hepatocytes confers altered regulation of glycogen," *J. Biol. Chem.*, 267:25129-25134, 1992.
Gopal, "Gene transfer method for transient gene expression, stable transfection, and cotransfection of suspension cell cultures," *Mol. Cell Biol.*, 5:1188-1190, 1985.
Graham and Prevec, "Adenovirus-based expression vectors and recombinant vaccines," *Biotechnology*, 20:363-390, 1992.
Graham and Prevec, "Manipulation of adenovirus vector," In: *Methods in Molecular Biology: Gene Transfer and Expression Protocol*, E. J. Murray (ed.), Clifton, N.J.: Humana Press, 7:109-128, 1991.
Graham and van der Eb, "A new technique for the assay of infectivity of human adenovirus 5 DNA", *Virology*, 52:456-467, 1973.
Graham et al., "Characteristics of a human cell line transformed by DNA from human adenovirus type 5", *J. Gen. Virol.*, 36:59-72, 1977.
Grunhaus and Horwitz, "Adenovirus as cloning vector," *Seminar in Virology*, 3:237-252, 1992.
Hall, Jacobsen, Winzor, "Stabilizing effect of sucrose against irreversible denaturation of rabbit muscle lactate dehydrogenase," *Biophys. Chem.*, 57(1):47-54, 1995.

Haskell and Bowen, "Efficient production of transgenic cattle by retroviral infection of early embryos," *Mol. Reprod. Dev.*, 40(3):386-390, 1995.

Hay et al., *Journal of Molecular Biology*, 175:493-510, 1984.

Hearing and Shenk, *Journal of Molecular Biology*, 167:809-822, 1983.

Hearing et al., *Journal of Virology*, 67:2555-2558, 1987.

Herman, Sinclair, Milton, Nail, "The effect of bulking agent on the solid-state stability of freeze-dried methylprednisolone sodium succinate," *Pharm. Res.*, 11(10):1467-1473, 1994.

Hermonat and Muzyczka, "Use of adeno-associated virus as a mammalian DNA cloning vector; transduction of neomycin resistance into mammalian tissue culture cells," *Proc. Natl. Acad. Sci. USA*, 81:6466-6470, 1984.

Hersdorffer et al., "Efficient gene transfer in live mice using a unique retroviral packaging line," *DNA Cell Biol.*, 9:713-723, 1990.

Herz and Gerard, "Adenovirus-mediated transfer of low density lipoprotein receptor gene acutely accelerates cholesterol clearance in normal mice," *Proc. Nat'l Acad. Sci. USA* 90:2812-2816, 1993.

Hollestein et al., *Science*, 253:49-53 1991.

Horwich et al. "Synthesis of hepadenovirus particles that contain replication-defective duck hepatitis B virus genomes in cultured HuH7 cells," *J. Virol.*, 64:642-650, 1990.

Hussussian et al., *Nature Genetics*, 15-21, 1994.

Jones and Shenk, "Isolation of deletion and substitution mutants of adenovirus type 5," *Cell*, 13:181-188, 1978.

Kamb et al., *Nature Genetics*, 8:22-26, 1994.

Kamb et al., *Science*, 2674:436-440, 1994.

Kaneda et al., *Science*, 243:375-378, 1989.

Kaplitt, Leone, Samulski, Siao, Pfaff, O'Malley, During, "Long-term gene expression and phenotypic correction suing adeno-associated virus vectors in the mammalian brain," *Nature Genetics*, 8:148-154, 1994.

Karlsson et al., *EMBO J.*, 5:2377-2385, 1986.

Kato et al., *J. Biol. Chem.*, 266:3361-3364, 1991.

Kaufman, "Selection and Coamplification of Heterologous Genes in Mammalian Cells," *Methods in Enzymology*, 185: 537-566, 1990.

Kelleher and Vos, "Long-term episomal gene delivery in human lymphoid cells using human and avian adenoviral-assisted transfection," *Biotechniques*, 17(6):1110-1117, 1994.

Kotin, Siniscalco, Samulski, Zhu, Hunter, McLaughlin, Muzyczka, Berns, "Site-specific integration by adeno-associated virus," *Proc. Natl. Acad. Sci. USA*, 87:2211-2215, 1990.

LaFace, Hermonat, Wakeland, Peck, "Gene transfer into hematopoietic progenitor cells mediated by an adeno-associated virus vector," *Virology*, 162:483-486, 1988.

Laughlin, Cardellichio, Coon, "Latent Infection of KB Cells with Adeno-Associated Virus Type 2," *J. Virol.*, 60:515-524, 1986.

Le Gal La Salle et al., "An adenovirus vector for gene transfer into neurons and glia in the brain," *Science*, 259:988-990, 1993.

Lebkowski, McNally, Okarma, and Lerch, "Adeno-associated virus: a vector system for efficient introduction and integration of DNA into a variety of mammalian cell types," *Mol. Cell. Biol.*, *:3988-3996, 1988.

Levrero et al., "Defective and nondefective adenovirus vectors for expressing foreign genes in vitro and in vivo," *Gene*, 101: 195-202, 1991.

Lin and Guidotti, *J. Biol. Chem.*, 264:14408-14414, 1989.

Lu, Stubbs, Culver, "Coat protein interactions involved in tobacco mosaic tobamovirus cross-protection," *Virology*, 248(2): 188-198, 1998.

Lueckel, Bodmer, Helk, Leuenberger, "Formulations of sugars with amino acids or mannitol—influence of concentration ratio on the properties of the freeze-concentrate and the lyophilizate," *Pharm. Dev. Technol.*, 3(3):326-336, 1998.

Luo, Zhou, Cooper, Munshi, Boswell, Broxmeyer, Srivastava, "Adeno-associated virus 2 mediated transfer and functional expression of a gene encoding the human granulocyte-macrophage colony-stimulating factor," *Blood*, 82 (Supp.): 1,303A, 1994.

Mann et al., "Construction of a retrovirus packaging mutant and its use to produce helper-free defective retrovirus," *Cell*, 33:153-159, 1983.

Markowitz et al., "A safe packaging line for gene transfer: Separating viral genes on two different plasmids," *J. Virol.*, 62:1120-1124, 1988.

Mathiowitz, Jacob, Jong, Carino, Chickering, Chaturvedi, Santos, Vijayaraghavan, Montgomery, Bassett, Morrell, "Biologically erodable microspheres as potential oral drug delivery systems," *Nature*, 386:410-414, 1998.

McLaughlin, Collis, Hermonat, Muzyczka, "Adeno-Associated Virus General Transduction Vectors Analysis of Proviral Structures," *J. Virol.*, 62:1963-1973, 1988.

Mercer, *Critic. Rev. Eukar. Gene Express.* 2:251-263, 1992.

Misselwitz, Hausdorf, Welfle, Hohne, Welfle, "Conformation and stability of recombinant HIV-1 capsid protein p24 (rp24)," *Biochim. Biophys. Acta*, 1250(1):9-18, 1995.

Montenarh, *Crit. Rev. Oncogen*, 3:233-256, 1992.

Mori et al., *Cancer Res.*, 54:3396-3397, 1994.

Muzyczka, "Use of Adeno-Associated Virus as a General Transduction Vector for Mammalian Cells," *Curr. Top. Microbiol. Immunol.*, 158:97-129, 1992.

Nakonechny and Teschke, "GroEL and GroES control of substrate flux in the in vivo folding pathway of phage P22 coat protein," *J. Biol. Chem.*, 273(42):27236-27244, 1998.

Nicolas and Rubinstein, "Retroviral vectors," In: *Vectors: A survey of molecular cloning vectors and their uses*, Rodriguez and Denhardt (eds.), Stoneham: Butterworth pp. 494-513, 1988.

Nicolau and Sene, *Biochim. Biophys. Acta*, 721:185-190, 1982.

Nicolau et al., *Methods Enzymol.*, 149:157-176, 1987.

Nobri et al., *Nature (London)*, 368:753-756, 1995.

Obrink, *BioEssays.*, 13:227-233, 1991.

Odin and Obrink, *Exp. Cell Res.*, 171:1-15, 1987.

Ohi, Dixit, Tillery, and Plonk, "Construction and replication of an adeno-associated virus expression vector that contains human λ-globin cDNA," *Gene*, 89L:279-28L, 1990.

Okamoto et al., *Proc. Natl. Acad. Sci. USA*, 91:11045-11049, 1994.

Orlow et al., *Cancer Res.*, 54:2848-2851, 1994.

Paskind et al., "Dependence of moloney murine leukemia virus production on cell growth," *Virology*, 67:242-248, 1975.

Pelletier and Sonenberg, *Nature*, 334:320-325, 1988.

Pennisi, E. "Training Viruses to Attack Cancers," *Science*, 282, 1998.

Perales et al., *Proc. Natl. Acad. Sci. USA*, 91:4086-4090, 1994.

Polissi, Goffin, Georgopoulos, "The *Escherichia coli* heat shock response and bacteriophage lambda development," *FEMS Microbiol. Rev.*, 17(1-2):159-169, 1995.

Potter et al., "Enhancer-dependent expression of human k immunoglobulin genes introduced into mouse pre-B lymphocytes by electroporation," *Proc. Nat'l Acad. Sci. USA*, 81:716'-7165, 1984.

Racher et al., *Biotechnology Techniques*, 9:169-174, 1995.

Ragot et al., "Efficient adenovirus-mediated transfer of a human minidystrophin gene to skeletal muscle of mdx mice," *Nature*, 361:647-650, 1993.

Renan, "Cancer genes: current status, future prospects, and applicants in radiotherapy/oncology," *Radiother. Oncol.*, 19:197-218, 1990.

Rich et al., "Development and analysis of recombinant adenoviruses for gene therapy of cystic fibrosis," *Hum. Gene Ther.*, 4:461-476, 1993.

Ridgeway, "Mammalian expression vectors," *In: Vectors: A survey of molecular cloning vectors and their uses*, Rodriguez R L, Denhardt DT, ed., Stoneham: Butterworth, pp. 467-492, 1988.

Rippe et al., "DNA-mediated gene transfer into adult rat hepatocytes in primary culture," *Mol. Cell. Biol.*, 10:689-695, 1990.

Rosenfeld et al., "Adenovirus-mediated transfer of a recombinant a1-antitrypsin gene to the lung epithelium in vivo," *Science*, 252:431-434, 1991.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079-9083, 1989.

Sagrera, Cobaleda, Berger, Marcos, Shnyrov, Villar, "Study of the influence of salt concentration on Newcastle disease virus matrix protein aggregation," *Biochem. Mol. Biol. Int.*, 46(3):429-435, 1998.

Samulski, Chang, Shenk, "Helper-free stocks of recombinant adeno-associated viruses: Normal integration does not require viral gene expression," *J. Virol.*, 63:3822-3828, 1989.

Samulski, Zhu, Xiao, Brook, Housman, Epstein, Hunter, "Targeted integration of adeno-associated virus (AAV) into human chromosome 19," *EMBO J.*, 10:3941-3950, 1991.

Santerre, et al., *Gene*, 30:147, 1984

Serrano et al., *Nature*, 366:704-707, 1993.

Serrano et al., *Science*, 267:249-252, 1995.

Shelling and Smith, "Targeted integration of transfected and infected adeno-associated virus vectors containing the neomycin resistance gene," *Gene Therapy*, 1:165-169, 1994.

Stratford-Perricaudet and Perricaudet, "Gene transfer into animals: the promise of adenovirus," *In: Human Gene Transfer*, Eds, O. Cohen-Haguenauer and M. Boiron, Editions John Libbey Eurotext, France, p. 51-61, 1991.

Stratford-Perricaudet et al., "Evaluation of the transfer and expression in mice of an enzyme-encoding gene using a human adenovirus vector," *Hum. Gene Ther.*, 1:241-256, 1990.

Takahashi et al., *Cancer Res.*, 52:2340-2342, 1992.

Temin, "Retrovirus vectors for gene transfer: Efficient integration into and expression of exogenous DNA in vertebrate cell genome," *In: Gene Transfer*, Kucherlapati (ed.), New York, Plenum Press, pp. 149-188, 1986.

Temin, In: Kucherlapati R, ed. Gene transfer. New York: Plenum Press, pp. 149-188, 1986.

Tibbetts, *Cell*, 12:243-249, 1977.

Top et al., "Immunization with live types 7 and 4 adenovirus vaccines. II. Antibody response and protective effect against acute respiratory disease due to adenovirus type 7," *J. Infect. Dis.*, 124:155-160, 1971.

Tratschin, Miller, Smith, Carter, "Adeno-associated virus vector for high-frequency integration, expression and rescue of genes in mammalian cells," *Mol. Cell. Biol.*, 5:32581-3260, 1985.

Tratschin, West, Sandbank, Carter, "A human parvovirus, adeno-associated virus, as a eucaryotic vector: transient expression and encapsidation of the procaryotic gene for chloramphenicol acetyltransferase," *Mol. Cell. Biol.*, 4:2072-2081, 1984.

Vanlandschoot, Beirnaert, Grooten, Jou, Fiers, "pH-dependent aggregation and secretion of soluble monomeric influenza hemagglutinin," *Arch. Virol.*, 143(2):227-239, 1998.

Vossen and Fried, "Sequestration stabilizes lac repressor-DNA complexes during gel electrophoresis," *Anal. Biochem.*, 245(1):85-92, 1997.

Wagner et al., *Proc. Nat'l. Acad. Sci.*, 87(9):34110-3414, 1990.

Wagner et al., *Science*, 260:1510-1513, 1993.

Wahlstrom et al., *Mol. Endrocrinol.*, 6:1013-1022, 1992.

Walsh, Nienhuis, Samulski, Brown, Miller, Young, Liu, "Phenotypic correction of Fanconi anemia in human hematopoietic cells with a recombinant adeno-associated virus vector," *Proc. Natl. Acad. Sci. USA*, 89:7257-7261, 1994; *J. Clin. Invest.*, 94:1440-1448, 1994.

Wang et al., In: Animal Cell Technology: Basic & Applied Aspects, S. Kaminogawa et al., (eds), vol. 5, pp 463-469, Kluwer Academic Publishers, Netherlands, 1993.

Wang et al., *Cytotechnology*, 9:41-49, 1992.

Wang et al., Proceeding of the Japanese Society for Animal Cell Technology, 1994.

Watanabe, M., Shirayoshi, Y., Koshimizu, U., Hashimoto, S., Yonehara, S., Eguchi, Y., Tsujimoto, Y. and Nakatsuji, N., "Gene transfection of mouse primordial germ cells in vitro and analysis of their survival and growth control," *Exp. Cell Res.* 230:76-83, 1997.

Wei, Wei, Samulski, Barranger, "Expression of the human glucocerebrosidase and arylsulfatase A genes in murine and patient primary fibroblasts transduced by an adeno-associated virus vector," *Gene Therapy*, 1:261-268, 1994.

Weinberg, R. A., *Science*, 254:1138-1146, 1991.

Wetzel, R., "Priciples of Protein Engineering. Part 2-Enhanced Folding and Stabilization of Proteins by Suppression of Aggregation in vitro and in vivo." *Protein Engineering. A Practical Approach*, chapter 8: 191-219, 1992. IRL Press, Oxford.

Wu and Wu, *J. Biol. Chem.*, 262:4429-4432, 1987.

Wu and Wu, "Evidence for targeted gene delivery to HepG2 hepatoma cells in vitro," *Biochemistry*, 27:887-892, 1988.

Wu and Wu, "Receptor-mediated in vitro gene transfections by a soluble DNA carrier system," *J. Biol. Chem.*, 262: 4429-4432, 1987.

Wu and Wu, *Adv. Drug Delivery Rev.*, 12:159-167, 1993.

Wu and Wu. *Biochemistry*, 27:887-892, 1988.

Yang et al., *Proc. Nat'l Acad Sci. USA*, 87:9568-9572, 1990.

Yang, Chen, Trempe, "Characterization of cell lines that inducibly express the adeno-associated virus Rep proteins," *J. Virol.*, 68:4847-4856, 1994.

Yoder, Kang, Zhou, Luo, Srivastava, "In vivo gene transfer in murine hematopoietic reconstituting stem cells mediated by the adeno-associated virus 2-based vectors," *Blood*, 82 (Supp.): 1:347 A, 1994.

Zhou, Broxmyer, Cooper, Harrington, Srivastava, "Adeno-associated virus 2 mediated gene transfer in murine hematopoietic cells, *Exp. Hematol.* (*NY*), 21:928-933, 1993.

Zhou, Cooper, Kang, Ruggieri, Heimfeld, Srivastava, Broxmeyer, "Adeno-associated virus 2-mediated high efficiency gene transfer into immature and mature subsets of hematopoietic progenitor cells in human umbilical cord blood," *J. Exp. Med*, 179:1867-1875, 1994.

What is claimed is:

1. A method for the preparation of a long-term storage stable adenovirus liquid formulation, comprising providing adenovirus and combining said adenovirus with a solution comprising a buffer and a polyol, whereby said adenovirus liquid formulation retains high infectivity.

2. The method of claim 1, wherein the adenovirus liquid formulation retains an infectivity of about 70% PFU/mL to about 99.9% PFU/mL of the starting infectivity when stored for six months at 4 centigrade.

3. The method of claim 1, wherein the polyol is at a concentration of from about 5% to about 30% (w/v).

4. The method of claim 1, wherein the polyol is glycerol, propylene glycol, polyethylene glycol, sorbitol, or mannitol.

5. The method of claim 4, wherein the polyol is glycerol.

6. The method of claim 1, wherein the buffer is at a concentration of from about 1 mM to 50 mM.

7. The method of claim 6, wherein the buffer is at a concentration of from about 5 mM to about 20 mM.

8. The method of claim 1, wherein the buffer is Tris-HCl, TES, HEPES, mono-Tris, brucine tetrahydrate, EPPS, tricine, histidine, or PBS.

9. The method of claim 8, wherein the buffer is Tris-HCl.

10. The method of claim 8, wherein the buffer is PBS.

11. The method of claim 1, wherein the polyol is glycerol and the buffer is Tris-HCl.

12. The method of claim 1, wherein the polyol is glycerol and the buffer is PBS.

13. The method of claim 1, wherein the polyol is at a concentration of from about 5% to about 30% (w/v) and the buffer is at a concentration of from about 5 mM to about 20 mM.

14. The method of claim 13, wherein the polyol is glycerol and the buffer is Tris-HCl.

15. The method of claim 13, wherein the polyol is glycerol and the buffer is PBS.

16. A method for the preparation of a long-term storage stable adenovirus liquid formulation, comprising providing adenovirus and combining said adenovirus with a solution comprising a buffer, a polyol, and a non-ionic detergent, whereby said adenovirus liquid formulation retains high infectivity.

17. The method of claim 16, wherein the non-ionic detergent is Tween-20 or Tween-80.

18. The method of claim 17, wherein the non-ionic detergent is Tween-80.

19. The method of claim 17, wherein the polyol is glycerol.

20. The method of claim 19, wherein the buffer is Tris-HCl.

21. The method of claim 19, wherein the buffer is PBS.

22. A method for the preparation of a long-term storage stable adenovirus liquid formulation, comprising providing adenovirus and combining said adenovirus with a solution comprising a buffer, a polyol; and a salt selected from the group consisting of $MgCl_2$, $MnCl_2$, $CaCl_2$, $ZnCl_2$, NaCl, and KCl, whereby said adenovirus liquid formulation retains high infectivity.

23. The method of claim 22, wherein the salt is $MgCl_2$.

* * * * *

UNITED STATES PATENT AND TRADEMARK OFFICE
CERTIFICATE OF CORRECTION

| | |
|---|---|
| PATENT NO. | : 7,888,097 B2 |
| APPLICATION NO. | : 11/926854 |
| DATED | : February 15, 2011 |
| INVENTOR(S) | : Zheng Wu et al. |

Page 1 of 1

It is certified that error appears in the above-identified patent and that said Letters Patent is hereby corrected as shown below:

In claim 19, column 58, line 23, delete "claim 17" and insert -- claim 18 -- therefor.

In claim 22, column 58, line 29, delete "polyol;" and insert -- polyol, -- therefor.

Signed and Sealed this
Fourteenth Day of June, 2011

David J. Kappos
*Director of the United States Patent and Trademark Office*

(12) EX PARTE REEXAMINATION CERTIFICATE (9990th)
United States Patent
Wu et al.

(10) Number: US 7,888,097 C1
(45) Certificate Issued: Dec. 20, 2013

(54) FORMULATION FOR ADENOVIRUS STORAGE

(75) Inventors: Zheng Wu, Sugar Land, TX (US); Shuyuan Zhang, Sugar Land, TX (US)

(73) Assignee: Crucell Holland B.V., Leiden (NL)

Reexamination Request:
No. 90/012,467, Sep. 6, 2012

Reexamination Certificate for:
Patent No.: 7,888,097
Issued: Feb. 15, 2011
Appl. No.: 11/926,854
Filed: Oct. 29, 2007

Certificate of Correction issued Jun. 14, 2011

Related U.S. Application Data

(60) Division of application No. 11/768,796, filed on Jun. 26, 2007, now Pat. No. 7,888,096, which is a continuation of application No. 09/941,296, filed on Aug. 28, 2001, now Pat. No. 7,235,391, which is a division of application No. 09/441,410, filed on Nov. 16, 1999, now Pat. No. 6,689,600.

(60) Provisional application No. 60/133,116, filed on May 7, 1999, provisional application No. 60/108,606, filed on Nov. 16, 1998.

(51) Int. Cl.
*C12N 1/04* (2006.01)
*C12N 7/00* (2006.01)

(52) U.S. Cl.
USPC ........ 435/235.1; 435/239; 435/260; 435/243; 435/320.1

(58) Field of Classification Search
None
See application file for complete search history.

(56) References Cited

To view the complete listing of prior art documents cited during the proceeding for Reexamination Control Number 90/012,467, please refer to the USPTO's public Patent Application Information Retrieval (PAIR) system under the Display References tab.

*Primary Examiner* — Bruce Campell

(57) ABSTRACT

The present invention addresses the need to improve the long-term storage stability (i.e. infectivity) of vector formulations. In particular, it has been demonstrated that for adenovirus, the use of bulking agents, cryoprotectants and lyoprotectants imparts desired properties that allow both lyophilized and liquid adenovirus formulations to be stored at 4° C. for up to 6 months and retain an infectivity between 60-100% of the starting infectivity.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 10 and 21 are cancelled.

Claims 1, 8, 12, 15, 16, 22 and 23 are determined to be patentable as amended.

Claims 3-7, 9, 11, 13, 14 and 17-20, dependent on an amended claim, are determined to be patentable.

1. A method for the preparation of a long-term storage stable adenovirus liquid formulation, comprising providing adenovirus and combining said adenovirus with a solution comprising a buffer, *a sugar,* and a polyol, whereby said adenovirus liquid formulation retains high infectivity, *wherein the adenovirus liquid formulation retains an infectivity of about 70% PFU/mL to about 99.9% PFU/mL of the starting infectivity when stored for six months at 4 degrees centigrade.*

8. The method of claim 1, wherein the buffer is Tris-HCl, TES, HEPES, mono-Tris, brucine tetrahydrate, EPPS, tricine, *or* histidine [or PBS].

12. The method of claim 1, wherein the polyol is [glycerol] *mannitol* and the buffer is [PBS] *Tris-HCl*.

15. The method of claim 13, wherein the polyol is [glycerol] *mannitol* and the buffer is [PBS] *Tris-HCl*.

16. [A] *The* method [for the preparation of a long-term storage stable adenovirus liquid formulation, comprising providing adenovirus and combining said adenovirus with a solution comprising a buffer, a polyol, and a non-ionic detergent, whereby said adenovirus liquid formulation retains high infectivity] *of claim 1, wherein the solution further comprises a non-ionic detergent.*

22. [A method for the preparation of a long-term storage stable adenovirus liquid formulation, comprising providing adenovirus and combining said adenovirus with a solution comprising a buffer, a polyol, and] *The method of claim 1, wherein the solution further comprises* a salt selected from the group consisting of MgCl$_2$, MnCl$_2$, CaCl$_2$, ZnCl$_2$, NaCl, and KCl[, whereby said adenovirus liquid formulation retains high infectivity].

23. The method of claim [22] *1*, wherein the [salt is MgCl$_2$] *sugar is selected from sucrose, dextrose, lactose, trehalose, glucose, and maltose*.

\* \* \* \* \*